US010751410B2

(12) United States Patent
Smith et al.

(10) Patent No.: US 10,751,410 B2
(45) Date of Patent: Aug. 25, 2020

(54) IMMUNOGENIC MIDDLE EAST RESPIRATORY SYNDROME CORONAVIRUS (MERS-COV) COMPOSITIONS AND METHODS

(71) Applicant: NOVAVAX, INC., Gaithersburg, MD (US)

(72) Inventors: Gale Smith, Gaithersburg, MD (US); Ye Liu, Gaithersburg, MD (US); Michael Massare, Gaithersburg, MD (US)

(73) Assignee: Novavax, Inc., Gaithersburg, MD (US)

(*) Notice: Subject to any disclaimer, the term of this patent is extended or adjusted under 35 U.S.C. 154(b) by 0 days.

(21) Appl. No.: 15/023,629

(22) PCT Filed: Sep. 19, 2014

(86) PCT No.: PCT/US2014/056517
§ 371 (c)(1),
(2) Date: Mar. 21, 2016

(87) PCT Pub. No.: WO2015/042373
PCT Pub. Date: Mar. 26, 2015

(65) Prior Publication Data
US 2016/0206729 A1 Jul. 21, 2016

Related U.S. Application Data

(60) Provisional application No. 61/880,111, filed on Sep. 19, 2013.

(51) Int. Cl.
| | | |
|---|---|---|
| *C12N 7/00* | (2006.01) |
| *A61K 39/145* | (2006.01) |
| *A61K 9/00* | (2006.01) |
| *A61K 9/127* | (2006.01) |
| *A61K 9/51* | (2006.01) |
| *A61K 39/215* | (2006.01) |
| *A61K 39/12* | (2006.01) |
| *A61K 39/42* | (2006.01) |
| *C07K 14/005* | (2006.01) |
| *C07K 16/10* | (2006.01) |
| *A61K 39/00* | (2006.01) |

(52) U.S. Cl.
CPC ............ *A61K 39/215* (2013.01); *A61K 39/12* (2013.01); *A61K 39/42* (2013.01); *C07K 14/005* (2013.01); *C07K 16/10* (2013.01); *C12N 7/00* (2013.01); *A61K 2039/505* (2013.01); *A61K 2039/5258* (2013.01); *A61K 2039/552* (2013.01); *A61K 2039/575* (2013.01); *C07K 2317/92* (2013.01); *C12N 2770/20022* (2013.01); *C12N 2770/20034* (2013.01); *C12N 2770/20071* (2013.01)

(58) Field of Classification Search
CPC .......... A61K 2039/53; A61K 2039/545; A61K 2039/55555; A61K 39/12; A61K 39/39
See application file for complete search history.

(56) References Cited

FOREIGN PATENT DOCUMENTS

| CN | 1472332 A | 2/2004 |
|---|---|---|
| RU | 2403063 C1 | 11/2010 |
| WO | WO 2004/085633 A1 | 10/2004 |
| WO | WO 2009/081285 A2 | 7/2009 |

OTHER PUBLICATIONS

Liu et al. Chimeric severe acute respiratory syndrome coronavirus (SARS-CoV) S glycoprotein and influenza matrix 1 efficiently form virus-like particles (VLPs) that protect mice against challenge with SARS-CoV. Vaccine, 2011; 29: 6606-6613.*
Van Boheemen S, et al. 2012. Genomic characterization of a newly discovered coronavirus associated with acute respiratory distress syndrome in humans. mBio 3(6): e00473-12. doi:10.1128/mBio.00473-12: pp. 1-9.*
S. Shimizu. Chapter 32: Routes of Adminitration. The Laboratory Mouse. Copyright 2004 Elsevier ISBN 0-1233-6425-6: 527-541.*
Lu et al. Immune responses against severe acute respiratory syndrome coronavirus induced by virus-like particles in mice. Immunol. 2007; 122: 496-502.*
Du et al. The spike protein of SARS-CoV—a target for vaccine and therapeutic development. Nat Rev Microbiol. 2009; 7(3): 226-236.*
Lövgren Bengtsson et al. ISCOM technology-based Matrix M™ adjuvant: success in future vaccines relies on formulation, Expert Review of Vaccines, 2011; 10:4: 401-403.*
Anonymous, "Stifel 2013 Healthcare Conference," pp. 1-35, http://www.novavax.com/download/file/2013_09_12%20Novavax_Stifel_presentation.pdf (2013).
Anonymous, "Novavax to Present at the 2013 Stifel Nicolaus Healthcare Conference," Reuters, 1 page http://in.reuters.com/article/2013/09/05/idUSnGNX7PTmrq+1d8+GNW20130905 (2013).
Cheng et al., "Use of convalescent plasma therapy in SARS patients in Hong Kong," Eur. J. Clin. Microbiol. Infect. Dis. 24(1):44-46 (2005).
Coleman et al., "Purified coronavirus spike protein nanoparticles induce coronavirus neutralizing antibodies in mice," Vaccine 32(26):3169-3174 (2014).
Database UniProt [Online], "SubName: Full=S Protein {ECO:0000313|EMBL:AGN70973.1}," EBI accesion No. UNIPROT:R9UQ53, Database accession No. R9UQ53 (2013).

(Continued)

*Primary Examiner* — Barry A Chestnut
(74) *Attorney, Agent, or Firm* — Cooley LLP

(57) ABSTRACT

Disclosed herein are nanoparticles containing MERS virus proteins in polymer structures, and compositions containing the nanoparticles formulated for administration as immunogenic compositions. Also provided herein are vector constructs encoding the proteins, and host cells containing the vector constructs. The disclosure also includes methods of making the nanoparticles and administering them to vertebrates, including methods of inducing immune responses to MERS that reduce or prevent infection by the virus.

18 Claims, 16 Drawing Sheets
Specification includes a Sequence Listing.

(56) References Cited

OTHER PUBLICATIONS

Du et al., "Identification of a Receptor-Binding Domain in the S Protein of the Novel Human Coronavirus Middle East Respiratory Syndrome Coronavirus as an Essential Target for Vaccine Development," J. Virol. 87(17):9939-9942 (2013).
Gillim-Ross et al., "Emerging Respiratory Viruses: Challenges and Vaccine Strategies," Clin. Microbiol. Rev. 19(4):614-636 (2006).
Hilgenfeld et al., "From SARS to MERS: 10 years of research on highly pathogenic human coronaviruses," Antiviral Res. 100(1):286-295 (2013).
International Preliminary Report on Patentability, PCT appl. No. PCT/US2014/056517, 12 pages (dated Mar. 22, 2016).
International Search Report, PCT appl. No. PCT/US2014/056517, 7 pages (dated Jan. 19, 2015).
Kuroiwa et al., "Antigen-specific human polyclonal antibodies from hyperimmunized cattle," Nat. Biotechnol. 27(2):173-181 (2009).
Liu et al., "Chimeric severe acute respiratory syndrome coronavirus (SARS-CoV) S glycoprotein and influenza matrix 1 efficiently form virus-like particles (VLPs) that protect mice against challenge with SARS-CoV," Vaccine 29(38):6606-6613 (2011).
Matsushita et al., "Triple immunoglobulin gene knockout transchromosomic cattle: bovine lambda cluster deletion and its effect on fully human polyclonal antibody production," PLOS One 9(3):1-14 (2014).
Parrish, "Novavax creates MERS-CoV vaccine candidate," http://vaccinenewsdaily.com/vaccine_development/325407-novavax-creates-mers-cov-vaccine-candidate/ (2013).
Poulsen et al., "Limits for Antibody Affinity Maturation and Repetoire Diversification in Hypervaccinated Humans," J. Immunol. 187(8):4429-4235 (2011).
Song et al., "Middle East Respiratory Syndrome Coronavirus Spike Protein Delivered by Modified Vaccinia Virus Ankara Efficiently Induces Virus-Neutralizing Antibodies," J. Virol. 87(21):11950-11954 (2013).
Written Opinion of the International Searching Authority, PCT appl. No. PCT/US2014/056517, 11 pages (dated Jan. 19, 2015).
Yeh, "Experience of using convalescent plasma for severe acute respiratory syndrome among healthcare workers in a Taiwan hospital," J. Antimicrob. Chemother. 56(5):919-922 (2005).
Jiang, et al., "A predicted receptor-binding and critical neutralizing domain in S protein of the novel human coronavirus HCoV-EMC", Journal of Infection (66):464-466 (2013).
Duan, et al., "An overview of the novel coronavirus MERS-CoV," Chin J Viral Dis, 3(4):245-249 (2013).
Delmas and Laude, "Assembly of Coronavirus Spike Protein into Trimers and Its Role in Epitope Expression," Journal of Virology 64(11):5367-5375 (1990).
Kam et al., "Antibodies against trimeric S glycoprotein protect hamsters against SARS-CoV challenge despite their capacity to mediate FcgammaRII-dependent entry into B cells in vitro," Vaccine 25(4):729-740 (2007).
Li et al., "Immunogenicity and Protection Efficacy of Monomeric and Trimeric Recombinant SARS Coronavirus Spike Protein Subunit Vaccine Candidates," Viral Immunology 26(2):126-132 (2013).

\* cited by examiner

FIGURES

Figure 1 Coronavirus Structure

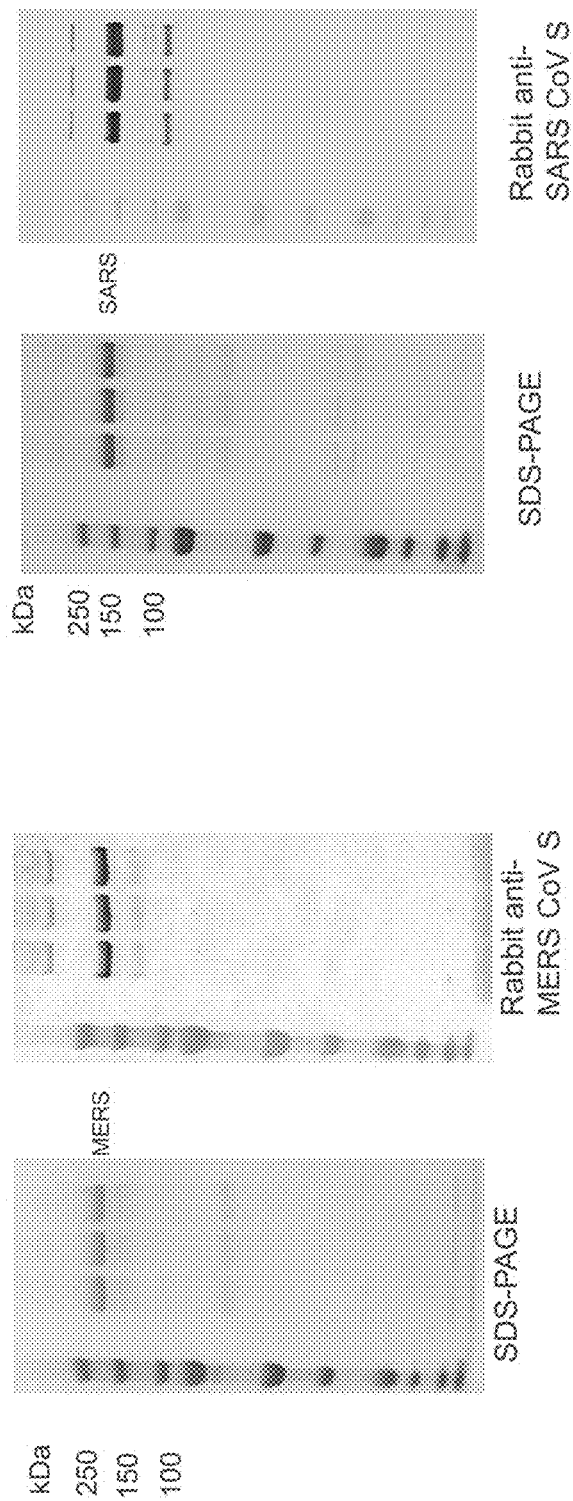
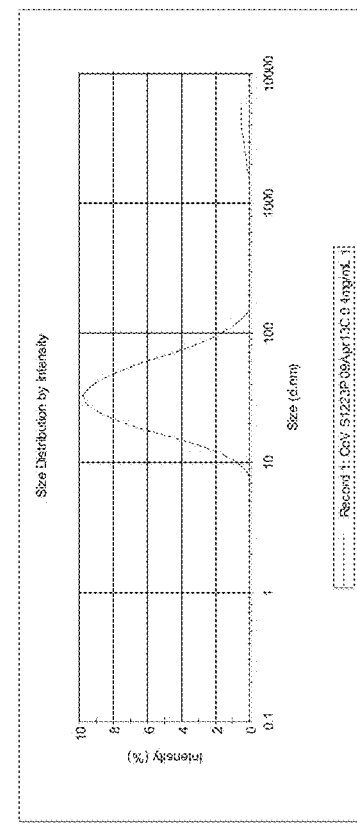
Figure 3

Figure 4

Electron Microscopy: MERS and SARS CoV S Nanoparticles

MERS CoV Spike (S)

26.0 nm

SARS CoV Spike (S)

MERS-CoV Mouse Immunogenicity

Study Design

| Group | Purified S Antigen | Dose (µg) | Alum Adjuvant (25 µg) | Matrix M1 Adjuvant (5 µg) | N/Group | Immunization (days) | Blood Draw (days) |
|---|---|---|---|---|---|---|---|
| 1 | MERS-CoV | 10.0 | - | - | 10 | 0, 14 | 0, 21, 45 |
| 2 | | 3.0 | - | - | 10 | 0, 14 | 0, 21, 45 |
| 3 | | 1.0 | - | - | 10 | 0, 14 | 0, 21, 45 |
| 4 | | 3.0 | + | - | 10 | 0, 14 | 0, 21, 45 |
| 5 | | 1.0 | + | - | 10 | 0, 14 | 0, 21, 45 |
| 6 | | 3.0 | - | + | 10 | 0, 14 | 0, 21, 45 |
| 7 | | 1.0 | - | + | 10 | 0, 14 | 0, 21, 45 |
| 8 | SARS-CoV | 3.0 | + | - | 10 | 0, 14 | 0, 21, 45 |
| 9 | | 3.0 | - | + | 10 | 0, 14 | 0, 21, 45 |
| 10 | | 3.0 | - | - | 10 | 0, 14 | 0, 21, 45 |

Time Line

D0 — D14 — D21 — D45

Immunize — Boost — Blood Draw — Blood Draw ⟶ MERS, SARS CoV Neutralizing Ab

Figure 6

MERS-CoV Al-Hasa_1_2013 Nanoparticle Vaccine Candidate

Genetic Engineering → Expression/Purification → MERS S Nanoparticles

MERS CoV Spike (S) gene

SDS-PAGE / Rabbit anti-MERS CoV S

MERS Spike (S) 26nm particles

Recombinant baculovirus – full length, codon optimized MERS S → Manufacturing Sf9 insect cells 10L – 1,000L scale bioreactors → Self-assembly of MERS S trimers; 26nm protein-protein micelles

Figure 7

MERS-CoV Spike Nanoparticles for Use as a Vaccine
Mouse Vaccination and Live Virus Microneutralization Assay of Mouse Sera Day 0 — Immunize
Day 14 — Boost
Day 21 — Blood Draw
Day 45 — Blood Draw Figure 8A: Codon Optimized sequence for MERS Al Hasa 1 spike protein (nucleotide sequence)

```
ATGATCCACTCCGTGTTCCTGTTGATGTTCCTGTTGACTCCTACCGAAAGCTACGTTGAT
GTTGGTCCAGATTCCGTGAAGAGCGCCTGCATCGAGGTGGATATCCAGCAAACATTCTTC
GACAAGACCTGGCCGAGGCCCATCGATGTCTCCAAGGCTGACGGTATCATCTACCCTCAG
GGCAGAACTTACTCTAACATCACTATCACATACCAAGGCCTGTTCCCATACCAGGGTGAC
CACGGCGATATGTACGTCTACAGCGCTGGACACGCTACCGGAACCACTCCTCAGAAGCTC
TTCGTTGCCAACTACTCACAGGACGTGAAGCAATTCGCTAACGGATTCGTGGTCCGTATC
GGTGCTGCCGCTAACAGCACCGGTACTGTGATCATCTCTCCAGCACTTCAGCCACAATC
CGCAAGATCTACCCTGCTTTCATGCTGGGTTCCTCTGTGGGCAACTTCTCCGATGGAAAG
ATGGGCAGGTTCTTCAACCACACTCTCGTCCTGCTCCCTGACGGCTGCGGAACATTGCTG
AGGGCCTTCTACTGTATCTTGGAGCCTAGATCTGGCAACCACTGCCCAGCTGGAAACAGC
TACACCTCATTCGCCACCTACCACACTCCAGCTACAGACTGTAGCGATGGTAACTACAAC
CGTAACGCTTCGTTGAACTCCTTCAAGGAATACTTCAACCTGCGCAACTGCACATTCATG
TACACCTACAACATCACTGAGGACGAAATCCTGGAGTGGTTCGGAATCACACAGACCGCC
CAAGGTGTTCACCTCTTCAGCTCACGTTACGTGGATTTGTACGGTGGCAACATGTTCCAG
TTCGCTACTCTCCCAGTCTACGACACAATCAAGTACTACTCCATCATCCCGCACTCTATC
CGTAGCATCCAATCAGACCGCAAGGCCTGGGCCGCTTTCTACGTCTACAAGCTGCAGCCT
CTCACCTTCCTCTTGGATTTCTCCGTTGACGGCTACATCCGTCGCGCTATCGATTGCGGA
TTCAACGACTTGTCTCAGCTGCACTGTTCGTACGAATCCTTCGACGTCGAGTCGGGAGTT
TACTCCGTGTCGTCCTTCGAGGCCAAGCCCTCGGGTTCCGTTGTGGAGCAAGCTGAGGGT
GTGGAGTGCGACTTCTCTCCTCTGCTCAGCGGTACTCCCCCTCAGGTCTACAACTTCAAG
CGTCTGGTTTTCACCAACTGCAACTACAACCTCACTAAGTTGCTGTCTTTGTTCAGCGTG
AACGACTTCACCTGCTCACAGATCTCGCCCGCCGCTATCGCTAGCAACTGTTACTCTAGC
CTGATCCTCGATTACTTCTCATACCCACTGTCCATGAAGTCTGACCTCAGCGTCTCATCG
GCCGGCCCGATCTCCCAATTCAACTACAAGCAGTCTTTCAGCAACCCTACCTGCTTGATC
CTGGCTACTGTGCCACACAACCTGACAACCATCACAAAGCCGCTCAAGTACTCTTACATC
AACAAGTGCTCAAGGCTCTTGTCGGACGATAGAACCGAAGTCCCACAACTGGTGAACGCT
AACCAGTACTCCCCTTGCGTCTCTATCGTTCCAAGCACCGTCTGGGAAGACGGCGATTAC
TACCGCAAGCAGCTCTCCCCCTTGGAGGGAGGTGGCTGGTTGGTGGCCTCAGGATCGACA
GTCGCTATGACCGAGCAGCTGCAAATGGGTTTCGGCATCACTGTGCAGTACGGTACTGAT
ACAAACTCCGTCTGCCCTAAGCTGGAATTCGCCAACGACACAAAGATCGCTTCTCAGCTG
GGTAACTGCGTGGAGTACTCCCTCTACGGCGTGTCTGGACGCGGTGTCTTCCAAAACTGT
ACTGCCGTCGGTGTTCGTCAGCAACGCTTCGTCTACGACGCTTACCAGAACCTCGTTGGT
TACTACTCCGACGATGGCAACTACTACTGCTTGAGGGCTTGTGTGTCCGTGCCCGTGTCC
GTGATCTACGACAAGGAAACCAAGACTCACGCCACCCTGTTCGGTAGCGTGGCTTGCGAG
CACATCTCCTCTACTATGTCACAATACTCCAGGTCTACAAGATCGATGCTCAAGAGGAGA
GACTCCACATACGGACCATTGCAGACCCCAGTGGGATGCGTCCTCGGTTTGGTGAACAGC
TCACTGTTCGTGGAAGATTGCAAGCTGCCCCTCGGCCAGTCCCTGTGTGCTCTCCCGGAC
ACCCCCTCTACATTGACCCCGCGTTCAGTTCGCTCGGTGCCCGGAGAGATGAGACTGGCT
TCCATCGCTTTCAACCACCCAATCCAGGTGGACCAATTGAACTCGTCCTACTTCAAGCTG
AGCATCCCGACAAACTTCTCATTCGGTGTCACCCAGGAGTACATCCAAACTACAATCCAG
AAGGTCACCGTTGACTGCAAGCAGTACGTGTGTAACGGCTTCCAAAAGTGCGAACAGCTG
CTCAGGGAGTACGGACAATTCTGTTCTAAGATCAACCAGGCCTTGCACGGTGCTAACCTG
CGTCAAGACGATTCTGTGCGCAACCTGTTCGCCAGCGTCAAGTCTAGCCAGTCATCGCCT
ATCATCCCAGGATTCGGTGGTGACTTCAACCTCACCTTGCTGGAACCTGTCAGCATCTCA
ACTGGTTCGAGGTCCGCCAGATCTGCTATCGAGGATCTCTTGTTCGACAAGGTGACCATC
GCTGACCCCGGCTACATGCAAGGATACGACGATTGCATGCAGCAAGGCCCTGCCAGCGCT
AGAGATCTGATCTGTGCCCAGTACGTTGCTGGATACAAGGTGTTGCCACCGCTGATGGAC
GTGAACATGGAAGCCGCTTACACCTCCTCCCTGCTGGGTTCCATCGCTGGCGTCGGATGG
```

Figure 8B: Codon Optimized sequence for MERS Al Hasa 1 spike protein

```
ACTGCTGGTCTCAGCTCATTCGCCGCTATCCCCTTCGCCCAAAGCATCTTCTACCGTTTG
AACGGTGTCGGCATCACTCAGCAAGTTTTGTCAGAGAACCAGAAGCTGATCGCTAACAAG
TTCAACCAAGCCCTGGGCGCTATGCAGACCGGATTCACCACTACAAACGAAGCCTTCCGT
AAGGTGCAAGACGCTGTCAACAACAACGCCCAGGCTCTCTCCAAGTTGGCCTCCGAGCTG
TCTAACACCTTCGGCGCCATCTCTGCTAGCATCGGAGATATCATCCAGCGTCTGGACGTG
CTCGAGCAGGATGCTCAAATCGACAGGCTGATCAACGGCAGATTGACCACTCTGAACGCC
TTCGTCGCTCAGCAACTCGTTAGATCAGAATCGGCTGCTCTGTCCGCTCAGCTCGCTAAG
GACAAGGTGAACGAGTGCGTGAAGGCCCAAAGCAAGCGTTCAGGTTTCTGTGGACAGGGC
ACCCACATCGTGTCTTTCGTCGTGAACGCTCCCAACGGTCTGTACTTCATGCACGTCGGC
TACTACCCTTCAAACCACATCGAGGTGGTCTCGGCCTACGGTCTCTGCGATGCCGCTAAC
CCGACTAACTGTATCGCTCCCGTGAACGGCTACTTCATCAAGACCAACAACACTCGCATC
GTGGACGAATGGTCCTACACCGGCTCGTCCTTCTACGCCCCTGAGCCAATCACTTCACTG
AACACAAAGTACGTCGCTCCCCACGTTACTTACCAGAACATCTCGACAAACTTGCCCCCT
CCATTGCTGGGTAACTCAACCGGCATCGACTTCCAAGATGAACTGGACGAGTTCTTCAAG
AACGTGTCCACATCTATCCCTAACTTCGGCTCCCTGACCCAGATCAACACAACCCTCTTG
GATCTCACTTACGAAATGTTGTCCCTGCAGCAAGTTGTGAAGGCCCTGAACGAATCTTAC
ATCGATCTCAAGGAGTTGGGAAACTACACCTACTACAACAAGTGGCCATGGTACATCTGG
CTCGGATTCATCGCTGGTTTGGTGGCCCTCGCTTTGTGCGTCTTCTTCATCCTGTGCTGT
ACCGGCTGCGGAACTAACTGTATGGGCAAGCTGAAGTGCAACCGTTGCTGTGATCGCTAC
GAGGAATACGACCTGGAGCCCCACAAGGTGCACGTCCACTAA
```

Figure 9: Codon Optimized sequence for MERS Al Hasa 1 spike protein (amino acid sequence)

```
>MERS_AlHasa1
    1 mihsvfllmf litptesyvd vgpdsvksac ievdiqqtff dktwprpidv skadgiiypq
   61 grtysnitit yqglfpyqgd hgdmyvysag hatgttpqkl fvanysqdvk qfangfvvri
  121 gaaanstgtv iispstsati rkiypafmlg ssvgnfsdgk mgrffnhtlv llpdgcgtll
  181 rafycilepr sgnhcpagns ytsfatyhtp atdcsdgnyn rnaslnsfke yfnlrnctfm
  241 ytynitedei lewfgitqta qqvhlfssry vdlyggnmfq fatlpvydti kyysiiphsi
  301 rsiqsdrkaw aafyvyklqp ltflldfsvd gyirraidcg fndlsqlhcs yesfdvesqv
  361 ysvssfeakp sgsvveqaeg vecdfsplis gtppqvynfk rlvftncnyn ltkllslfsv
  421 ndftcsqisp aaiasncyss lildyfsypl smksdlsvss agpisqfnyk qsfsnptcli
  481 latvphnltt itkplkysyi nkcsrllsdd rtevpqlvna nqyspcvsiv pstvwedgdy
  541 yrkqlspleg ggwlvasgst vamteqlqmg fgitvqygtd tnsvcpklef andtkiasql
  601 gncveyslyg vsgrgvfqnc tavgvrqqrf vydayqnlvg yysddgnyyc lracvsvpvs
  661 viydketkth atlfgsvace hisstmsqys rstrsmlkrr dstyqplqtp vgcvlglvns
  721 slfvedcklp lgqslcalpd tpstltprsv rsvpgemrla siafnhpiqv dqlnssyfkl
  781 siptnfsfgv tqeyiqttiq kvtvdckqyv cngfqkceql lreygqfcsk inqalhganl
  841 rqddsvrnlf asvkssqssp iipgfggdfn ltllepvsis tqsrsarsai edllfdkvti
  901 adpgymqgyd dcmqqgpasa rdlicaqyva gykvlpplmd vnmeaaytss llgsiagvgw
  961 taglssfaai pfaqsifyrl ngvgitqqvl senqkliank fnqalgamqt qftttneafr
 1021 kvqdavnnna qalsklasel sntfgaisas igdiiqrldv leqdaqidrl ingrlttlna
 1081 fvaqqlvrse saalsaqlak dkvnecvkaq skrsgfcgqg thivsfvvna pnglyfmhvg
 1141 yypsnhievv sayglcdaan ptnciapvng yfiktnntri vdewsytgss fyapepitsl
 1201 ntkyvaphvt yqnistnlpp pllgnstgid fqdeldeffk nvstsipnfg sltqinttll
 1261 dltyemlslq qvvkalnesy idlkelgnyt yynkwpwyiw lgfiaglval alcvffilcc
 1321 tgcgtncmgk lkcnrccdry eeydlephkv hvh
```

Figure 12

SEQUENCE LISTING

<160> NUMBER OF SEQ ID NOS: 2

<210> SEQ ID NO 1
<211> LENGTH: 4062
<212> TYPE: DNA
<213> ORGANISM: MERS-CoV

<400> SEQUENCE: 1

```
atgatccact ccgtgttcct gttgatgttc ctgttgactc ctaccgaaag ctacgttgat      60
gttggtccag attccgtgaa gagcgcctgc atcgaggtgg atatccagca aacattcttc     120
gacaagacct ggccgaggcc catcgatgtc tccaaggctg acggtatcat ctaccctcag     180
ggcagaactt actctaacat cactatcaca taccaaggcc tgttcccata ccagggtgac     240
cacggcgata tgtacgtcta cagcgctgga cacgctaccg gaaccactcc tcagaagctc     300
```

```
ttcgttgcca actactcaca ggacgtgaag caattcgcta acggattcgt ggtccgtatc    360
ggtgctgccg ctaacagcac cggtactgtg atcatctctc ccagcacttc agccacaatc    420
cgcaagatct accctgcttt catgctgggt tcctctgtgg gcaacttctc cgatggaaag    480
atgggcaggt tcttcaacca cactctcgtc ctgctccctg acggctgcgg aacattgctg    540
agggccttct actgtatctt ggagcctaga tctggcaacc actgcccagc tggaaacagc    600
tacacctcat cgccaccta ccacactcca gctacagact gtagcgatgg taactacaac    660
cgtaacgctt cgttgaactc cttcaaggaa tacttcaacc tgcgcaactg cacattcatg    720
tacacctaca acatcactga ggacgaaatc ctggagtggt tcggaatcac acagaccgcc    780
caaggtgttc acctcttcag ctcacgttac gtggatttgt acggtggcaa catgttccag    840
ttcgctactc tcccagtcta cgacacaatc aagtactact ccatcatccc gcactctatc    900
cgtagcatcc aatcagaccg caaggcctgg gccgctttct acgtctacaa gctgcagcct    960
ctcaccttcc tcttggattt ctccgttgac ggctacatcc gtcgcgctat cgattgcgga    1020
ttcaacgact tgtctcagct gcactgttcg tacgaatcct tcgacgtcga gtcgggagtt    1080
tactccgtgt cgtccttcga ggccaagccc tcgggttccg ttgtggagca agctgagggt    1140
gtggagtgcg acttctctcc tctgctcagc ggtactcccc ctcaggtcta caacttcaag    1200
cgtctggttt tcaccaactg caactacaac ctcactaagt tgctgtcttt gttcagcgtg    1260
aacgacttca cctgctcaca gatctcgccc gccgctatcg ctagcaactg ttactctagc    1320
ctgatcctcg attacttctc ataccccactg tccatgaagt ctgacctcag cgtctcatcg    1380
gccggcccga tctcccaatt caactacaag cagtctttca gcaaccctac ctgcttgatc    1440
ctggctactg tgccacacaa cctgacaacc atcacaaagc cgctcaagta ctcttacatc    1500
aacaagtgct caaggctctt gtcggacgat agaaccgaag tcccacaact ggtgaacgct    1560
aaccagtact ccccttgcgt ctctatcgtt ccaagcaccg tctgggaaga cggcgattac    1620
taccgcaagc agctctcccc cttggaggga ggtggctggt tggtggcctc aggatcgaca    1680
gtcgctatga ccgagcagct gcaaatgggt ttcggcatca ctgtgcagta cggtactgat    1740
acaaactccg tctgccctaa gctggaattc gccaacgaca caaagatcgc ttctcagctg    1800
ggtaactgcg tggagtactc cctctacggc gtgtctggac gcggtgtctt ccaaaactgt    1860
actgccgtcg gtgttcgtca gcaacgcttc gtctacgacg cttaccagaa cctcgttggt    1920
tactactccg acgatggcaa ctactactgc ttgagggctt gtgtgtccgt gcccgtgtcc    1980
gtgatctacg acaaggaaac caagactcac gccaccctgt tcggtagcgt ggcttgcgag    2040
cacatctcct ctactatgtc acaatactcc aggtctacaa gatcgatgct caagaggaga    2100
gactccacat acgaccatt gcagaccca gtgggatgcg tcctcggttt ggtgaacagc    2160
tcactgttcg tggaagattg caagctgccc ctcggccagt ccctgtgtgc tctcccggac    2220 acccctcta cattgacccc gcgttcagtt cgctcggtgc ccggagagat gagactggct    2280
tccatcgctt tcaaccaccc aatccaggtg gaccaattga actcgtccta cttcaagctg    2340
agcatcccga caaacttctc attcggtgtc acccaggagt acatccaaac tacaatccag    2400
aaggtcaccg ttgactgcaa gcagtacgtg tgtaacggtc tccaaaagtg cgaacagctg    2460
ctcagggagt acggacaatt ctgttctaag atcaaccagg ccttgcacgg tgctaacctg    2520
cgtcaagacg attctgtgcg caacctgttc gccagcgtca agtctagcca gtcatcgcct    2580
atcatcccag gattcggtgg tgacttcaac ctcaccttgc tggaacctgt cagcatctca    2640
```

```
actggttcga ggtccgccag atctgctatc gaggatctct tgttcgacaa ggtgaccatc    2700
gctgaccccg ctacatgca aggatacgac gattgcatgc agcaaggccc tgccagcgct    2760
agagatctga tctgtgccca gtacgttgct ggatacaagg tgttgccacc gctgatggac    2820
gtgaacatgg aagccgctta cacctcctcc ctgctgggtt ccatcgctgg cgtcggatgg    2880
actgctggtc tcagctcatt cgccgctatc cccttcgccc aaagcatctt ctaccgtttg    2940
aacggtgtcg gcatcactca gcaagttttg tcagagaacc agaagctgat cgctaacaag    3000
ttcaaccaag ccctgggcgc tatgcagacc ggattcacca ctacaaacga agccttccgt    3060
aaggtgcaag acgctgtcaa caacaacgcc aggctctct ccaagttggc ctccgagctg    3120
tctaacacct tcggcgccat ctctgctagc atcggagata tcatccagcg tctggacgtg    3180
ctcgagcagg atgctcaaat cgacaggctg atcaacggca gattgaccac tctgaacgcc    3240
ttcgtcgctc agcaactcgt tagatcagaa tcggctgctc tgtccgctca gctcgctaag    3300
gacaaggtga acgagtgcgt gaaggcccaa agcaagcgtt caggtttctg tggacagggc    3360
acccacatcg tgtctttcgt cgtgaacgct cccaacggtc tgtacttcat gcacgtcggc    3420 tactacccctt caaaccacat cgaggtggtc tcggcctacg gtctctgcga tgccgctaac    3480
ccgactaact gtatcgctcc cgtgaacggc tacttcatca agaccaacaa cactcgcatc    3540
gtggacgaat ggtcctacac cggctcgtcc ttctacgccc tgagccaat cacttcactg    3600 aacacaaagt acgtcgctcc ccacgttact taccagaaca tctcgacaaa cttgcccct    3660 ccattgctgg gtaactcaac cggcatcgac ttccagatg aactggacga gttcttcaag    3720
aacgtgtcca catctatccc taacttcggc tccctgaccc agatcaacac aaccctcttg    3780
gatctcactt acgaaatgtt gtccctgcag caagttgtga aggccctgaa cgaatcttac    3840
atcgatctca aggagttggg aaactacacc tactacaaca gtggccatg gtacatctgg    3900 ctcggattca tcgctggttt ggtggccctc gctttgtgcg tcttcttcat cctgtgctgt    3960
accggctgcg gaactaactg tatgggcaag ctgaagtgca accgttgctg tgatcgctac    4020
gaggaatacg acctggagcc ccacaaggtg cacgtccact aa    4062
```

<210> SEQ ID NO 2  
<211> LENGTH: 1353  
<212> TYPE: PRT  
<213> ORGANISM: MERS-CoV

<400> SEQUENCE: 2

```
Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
        115                 120                 125
```

```
Thr Val Ile Ile Ser Pro Ser Thr Ala Thr Ile Arg Lys Ile Tyr
    130                 135             140

Pro Ala Phe Met Leu Gly Ser Ser Val Gly Asn Phe Ser Asp Gly Lys
145             150                 155                 160

Met Gly Arg Phe Phe Asn His Thr Leu Val Leu Leu Pro Asp Gly Cys
                165                 170                 175

Gly Thr Leu Leu Arg Ala Phe Tyr Cys Ile Leu Glu Pro Arg Ser Gly
            180                 185                 190

Asn His Cys Pro Ala Gly Asn Ser Tyr Thr Ser Phe Ala Thr Tyr His
        195                 200                 205

Thr Pro Ala Thr Asp Cys Ser Asp Gly Asn Tyr Asn Arg Asn Ala Ser
    210                 215                 220

Leu Asn Ser Phe Lys Glu Tyr Phe Asn Leu Arg Asn Cys Thr Phe Met
225             230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
        275                 280                 285

Thr Ile Lys Tyr Tyr Ser Ile Ile Pro His Ser Ile Arg Ser Ile Gln
    290                 295                 300

Ser Asp Arg Lys Ala Trp Ala Ala Phe Tyr Val Tyr Lys Leu Gln Pro
305             310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
            340                 345                 350

Ser Phe Asp Val Glu Ser Gly Val Tyr Ser Val Ser Ser Phe Glu Ala
        355                 360                 365

Lys Pro Ser Gly Ser Val Val Glu Gln Ala Glu Gly Val Glu Cys Asp
    370                 375                 380

Phe Ser Pro Leu Leu Ser Gly Thr Pro Pro Gln Val Tyr Asn Phe Lys
385             390                 395                 400

Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
            420                 425                 430

Ile Ala Ser Asn Cys Tyr Ser Ser Leu Ile Leu Asp Tyr Phe Ser Tyr
        435                 440                 445

Pro Leu Ser Met Lys Ser Asp Leu Ser Val Ser Ser Ala Gly Pro Ile
    450                 455                 460

Ser Gln Phe Asn Tyr Lys Gln Ser Phe Ser Asn Pro Thr Cys Leu Ile
465             470                 475                 480

Leu Ala Thr Val Pro His Asn Leu Thr Thr Ile Thr Lys Pro Leu Lys
                485                 490                 495

Tyr Ser Tyr Ile Asn Lys Cys Ser Arg Leu Leu Ser Asp Asp Arg Thr
            500                 505                 510

Glu Val Pro Gln Leu Val Asn Ala Asn Gln Tyr Ser Pro Cys Val Ser
        515                 520                 525

Ile Val Pro Ser Thr Val Trp Glu Asp Gly Asp Tyr Tyr Arg Lys Gln
    530                 535                 540
```

```
Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
            565                 570                 575

Tyr Gly Thr Asp Thr Asn Ser Val Cys Pro Lys Leu Glu Phe Ala Asn
                580                 585                 590

Asp Thr Lys Ile Ala Ser Gln Leu Gly Asn Cys Val Glu Tyr Ser Leu
            595                 600                 605

Tyr Gly Val Ser Gly Arg Gly Val Phe Gln Asn Cys Thr Ala Val Gly
        610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
                645                 650                 655

Val Pro Val Ser Val Ile Tyr Asp Lys Glu Thr Lys Thr His Ala Thr
                660                 665                 670

Leu Phe Gly Ser Val Ala Cys Glu His Ile Ser Ser Thr Met Ser Gln
        675                 680                 685

Tyr Ser Arg Ser Thr Arg Ser Met Leu Lys Arg Arg Asp Ser Thr Tyr
        690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
                725                 730                 735

Ala Leu Pro Asp Thr Pro Ser Thr Leu Thr Pro Arg Ser Val Arg Ser
                740                 745                 750

Val Pro Gly Glu Met Arg Leu Ala Ser Ile Ala Phe Asn His Pro Ile
        755                 760                 765

Gln Val Asp Gln Leu Asn Ser Ser Tyr Phe Lys Leu Ser Ile Pro Thr
            770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Val Cys Asn Gly Phe Gln Lys
                805                 810                 815

Cys Glu Gln Leu Leu Arg Glu Tyr Gly Gln Phe Cys Ser Lys Ile Asn
                820                 825                 830

Gln Ala Leu His Gly Ala Asn Leu Arg Gln Asp Asp Ser Val Arg Asn
            835                 840                 845

Leu Phe Ala Ser Val Lys Ser Ser Gln Ser Ser Pro Ile Ile Pro Gly
850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
                885                 890                 895

Lys Val Thr Ile Ala Asp Pro Gly Tyr Met Gln Gly Tyr Asp Asp Cys
            900                 905                 910

Met Gln Gln Gly Pro Ala Ser Ala Arg Asp Leu Ile Cys Ala Gln Tyr
            915                 920                 925

Val Ala Gly Tyr Lys Val Leu Pro Pro Leu Met Asp Val Asn Met Glu
            930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
```

-continued

```
                965                 970                 975
Phe Tyr Arg Leu Asn Gly Val Gly Ile Thr Gln Gln Val Leu Ser Glu
            980                 985                 990
Asn Gln Lys Leu Ile Ala Asn Lys Phe Asn Gln Ala Leu Gly Ala Met
            995                1000                1005
Gln Thr Gly Phe Thr Thr Thr Asn Glu Ala Phe Arg Lys Val Gln
        1010                1015                1020
Asp Ala Val Asn Asn Ala Gln Ala Leu Ser Lys Leu Ala Ser
        1025                1030                1035
Glu Leu Ser Asn Thr Phe Gly Ala Ile Ser Ala Ser Ile Gly Asp
        1040                1045                1050
Ile Ile Gln Arg Leu Asp Val Leu Glu Gln Asp Ala Gln Ile Asp
        1055                1060                1065
Arg Leu Ile Asn Gly Arg Leu Thr Thr Leu Asn Ala Phe Val Ala
        1070                1075                1080
Gln Gln Leu Val Arg Ser Glu Ser Ala Ala Leu Ser Ala Gln Leu
        1085                1090                1095
Ala Lys Asp Lys Val Asn Glu Cys Val Lys Ala Gln Ser Lys Arg
        1100                1105                1110
Ser Gly Phe Cys Gly Gln Gly Thr His Ile Val Ser Phe Val Val
        1115                1120                1125
Asn Ala Pro Asn Gly Leu Tyr Phe Met His Val Gly Tyr Tyr Pro
        1130                1135                1140
Ser Asn His Ile Glu Val Val Ser Ala Tyr Gly Leu Cys Asp Ala
        1145                1150                1155
Ala Asn Pro Thr Asn Cys Ile Ala Pro Val Asn Gly Tyr Phe Ile
        1160                1165                1170
Lys Thr Asn Asn Thr Arg Ile Val Asp Glu Trp Ser Tyr Thr Gly
        1175                1180                1185
Ser Ser Phe Tyr Ala Pro Glu Pro Ile Thr Ser Leu Asn Thr Lys
        1190                1195                1200
Tyr Val Ala Pro His Val Thr Tyr Gln Asn Ile Ser Thr Asn Leu
        1205                1210                1215
Pro Pro Pro Leu Leu Gly Asn Ser Thr Gly Ile Asp Phe Gln Asp
        1220                1225                1230
Glu Leu Asp Glu Phe Phe Lys Asn Val Ser Thr Ser Ile Pro Asn
        1235                1240                1245
Phe Gly Ser Leu Thr Gln Ile Asn Thr Thr Leu Leu Asp Leu Thr
        1250                1255                1260
Tyr Glu Met Leu Ser Leu Gln Gln Val Val Lys Ala Leu Asn Glu
        1265                1270                1275
Ser Tyr Ile Asp Leu Lys Glu Leu Gly Asn Tyr Thr Tyr Tyr Asn
        1280                1285                1290
Lys Trp Pro Trp Tyr Ile Trp Leu Gly Phe Ile Ala Gly Leu Val
        1295                1300                1305
Ala Leu Ala Leu Cys Val Phe Phe Ile Leu Cys Cys Thr Gly Cys
        1310                1315                1320
Gly Thr Asn Cys Met Gly Lys Leu Lys Cys Asn Arg Cys Cys Asp
        1325                1330                1335
Arg Tyr Glu Glu Tyr Asp Leu Glu Pro His Lys Val His Val His
        1340                1345                1350
```

IMMUNOGENIC MIDDLE EAST RESPIRATORY SYNDROME CORONAVIRUS (MERS-COV) COMPOSITIONS AND METHODS

CROSS REFERENCE TO RELATED APPLICATIONS

This application is a national phase filing under 35 U.S.C. § 371 of International Patent Application No. PCT/US2014/056517, filed Sep. 19, 2014, which claims the benefit of U.S. Provisional Application No. 61/880,111, filed Sep. 19, 2013, the disclosures of which are herein incorporated by reference in their entirety for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: Seqlist.txt, date recorded: Sep. 18, 2014, file size 17,384 megabytes).

BACKGROUND

Coronaviruses can cause disease in animals such as humans. SARS (Severe Acute Respiratory Syndrome) is one example of such a disease. Recently, a new coronavirus has emerged, Middle East Respiratory Syndrome Coronavirus (MERS-CoV), which is associated with human fatalities. MERS-CoV has been identified as a "threat to global health" by the World Health Organization (WHO), and has been reported in 21 countries in the Middle East and Europe. MERS-CoV is a highly pathogenic respiratory virus that causes severe respiratory distress and potentially renal failure in infected individuals [1, 2].

Coronaviruses attach to the membrane of cells via interaction of their Spike (S) glycoproteins on the surface of the virion with their cognate receptor on host cells (e.g. dipeptidyl peptidase 4 (DPP4), found on a variety of human cells including lung and kidney cells). The S glycoprotein consists of an N-terminal S1 domain that contains the receptor binding domain (RBD) and an S2 domain responsible for virus-cell fusion. The MERS-CoV RBD consists of a core domain that has been co-crystallized with the human DPP4 protein, showing that it interacts with blades 4 and 5 of DPP4 [11]. In other coronaviruses, including SARS-CoV, antibodies to the RBD are able to neutralize and inhibit growth of the virus in vitro [12-14]. In mouse models of SARS-CoV, vaccine induced and passively transferred neutralizing antibodies have proven to be effective in inhibiting lung pathogenesis and death [15]. However, Antibody Dependent Enhancement (ADE) in human immune cells has been reported for SARS CoV in vitro though its clinical significance in vivo is unknown.

Human convalescent plasma and/or immunoglobulin has been used effectively to prevent and treat many viral infectious agents [16]. Public Health England and the International Severe Acute Respiratory & Emerging Infection Consortium (ISARIC) identified passive immunotherapy with neutralizing antibodies (including convalescent plasma) as a MERS-CoV treatment approach that warrants priority study. However, production of large quantities of anti-pathogen human plasma and/or immunoglobulin with high affinity and avidity antibodies currently requires donations by convalescent humans that can limit widespread availability of these human derived products for a number of cultural, infrastructure, and logistical reasons. Alternative means to rapidly produce specific human polyclonal immunoglobulin to prevent and treat infectious agents, including MERS-CoV, are needed.

SUMMARY

Disclosed herein are compositions and methods for simulating immune responses against infection by the coronavirus (CoV) that causes Middle East Respiratory Syndrome (MERS-CoV). The present disclosure provides compositions that are immunogenic and provide protection against MERS-CoV infection. Advantageously, the compositions induce neutralizing antibodies against MERS-CoV and can be used as vaccines.

The present disclosure also provides for a method of inducing substantial immunity to virus infection in an animal susceptible to MERS-CoV, comprising administering at least one effective dose of the vaccine comprising a MERS-CoV nanoparticle. In one embodiment, said method comprises administering to an animal said nanoparticle orally, intradermally, intranasally, intramuscularly, intraperitoneally, intravenously, or subcutaneously.

In aspects, the nanoparticle contains only one type of MERS-CoV protein. In particular aspects, the sole protein is a Spike (S) protein.

In one aspect, the disclosure provides an immunogenic composition comprising a MERS-CoV nanoparticle, wherein the nanoparticle comprises at least one trimer of a Spike polypeptide. In another embodiment, the nanoparticle comprises at least about five trimers to about 30 trimers of the Spike polypeptide. In another embodiment, the nanoparticle comprises at least about ten trimers to about 20 trimers of the Spike polypeptide. In one embodiment, the concentration of the nanoparticle is at least about 20 µg/mL to about 60 µg/mL. In another embodiment, the concentration of the nanoparticle is at least about 30 µg/mL to about 50 µg/mL. In a further embodiment, the Spike polypeptide comprises SEQ ID NO: 2. In yet a further embodiment, the Spike polypeptide consists of SEQ ID NO: 2.

In another aspect, the disclosure provides a method of producing a high affinity antibody comprising administering to an animal an immunogenic composition comprising a MERS-CoV nanoparticle, wherein the nanoparticle comprises at least one trimer of a Spike polypeptide, collecting serum and/or plasma from the animal, and purifying the antibody from the serum and/or plasma. In one embodiment, the method further comprises the administration of an adjuvant. In a further embodiment, the adjuvant is selected from the group consisting of Montanide ISA 206, Quil A, Alum, Freund's adjuvant, incomplete Freund's adjuvant, and aluminum hydroxide adjuvants. In one embodiment, the animal is bovine or equine. In a further embodiment, the bovine or equine animal is a transgenic animal.

In one embodiment, the antibody produced by immunization of an animal with the nanoparticle has a KD between $10^{-8}$ and $10^{-15}$. In a further embodiment, the antibody has a KD between about $10^{-12}$ and $10^{-14}$ or between about $10^{-13}$ and $10^{-14}$.

In yet another aspect, the disclosure comprises further administering the purified high affinity antibody produced by the method to a human subject.

BRIEF DESCRIPTION OF THE DRAWINGS

FIG. 3 illustrates binding of antibody to MERS CoV nanoparticle VLPs and SARS CoV nanoparticle VLPs disclosed herein by anti-MERS antibody and by anti SARS antibody respectively.

FIG. 4 illustrates electron micrographs of MERS CoV nanoparticle VLPs and SARS CoV nanoparticle VLPs disclosed herein.

FIG. 5 illustrates an immunization protocol for MERS CoV nanoparticle VLPs and SARS CoV nanoparticle VLPs disclosed herein at different time periods, different doses and with and without adjuvant.

FIG. 6 illustrates vaccine particles obtained by performing methods disclosed herein. The MERS Spike proteins are shown assembled in trimer of 26 nm protein-protein micelles.

FIG. 7 illustrates neutralization results following immunization of MERS CoV VLPs and SARS CoV nanoparticle VLPs disclosed herein into mice. The Matrix M adjuvant is especially effective.

FIG. 8 illustrates a codon-optimized MERS CoV Spike nucleotide sequence.

FIG. 9 illustrates a MERS CoV Spike amino acid sequence.

FIG. 12A-B shows MERS-CoV neutralization assays. Panel A shows SAB-300 and SAB-301 were tested for their ability to neutralize MERS-CoV by $TCID_{50}$ assay graphed as percent of virus titer compared to negative control purified hIgG. A higher percentage means less inhibition of infection. Panel B shows antibody dependent enhancement of SAB-300 and SAB-301 on MERS-CoV. RNA from MERS-CoV pre-incubated with SAB-300 and SAB-301 at 48 hours post infection was assayed for amount of MERS-CoV specific transcript, and graphed as fold change compared to mock samples. n. s. means not-significant.

DETAILED DESCRIPTION

Figure 1:
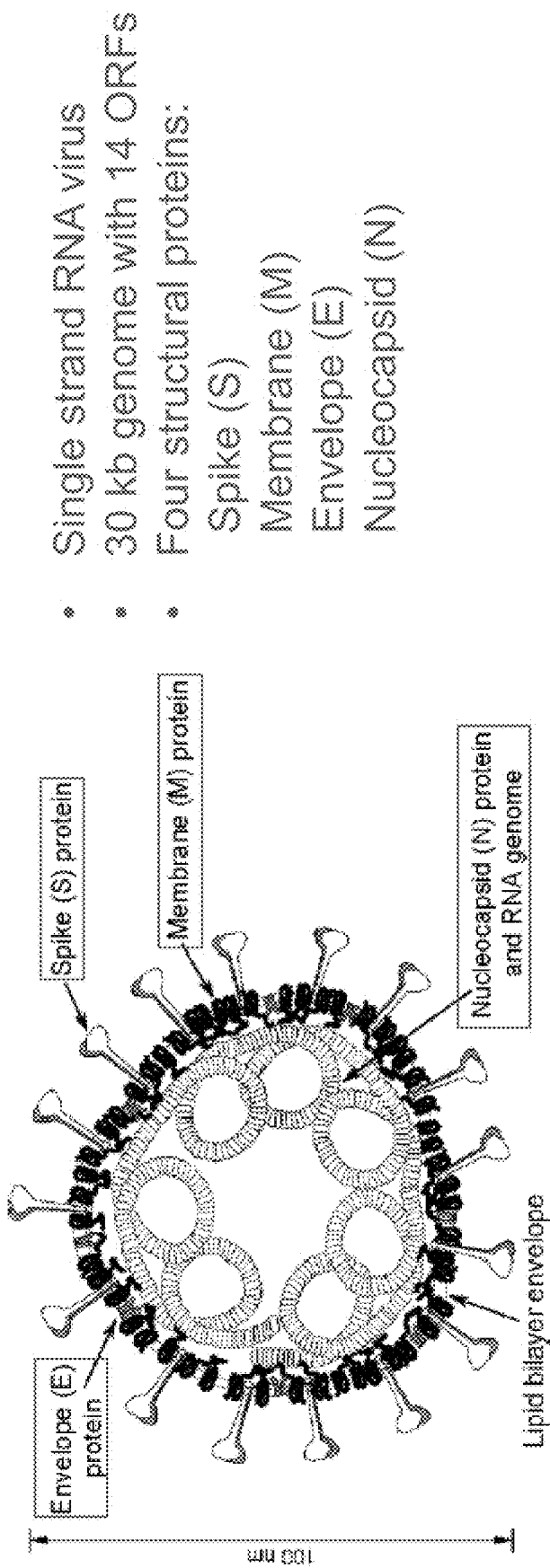
FIG. 1 illustrates the Coronavirus structure.
Figure 2:
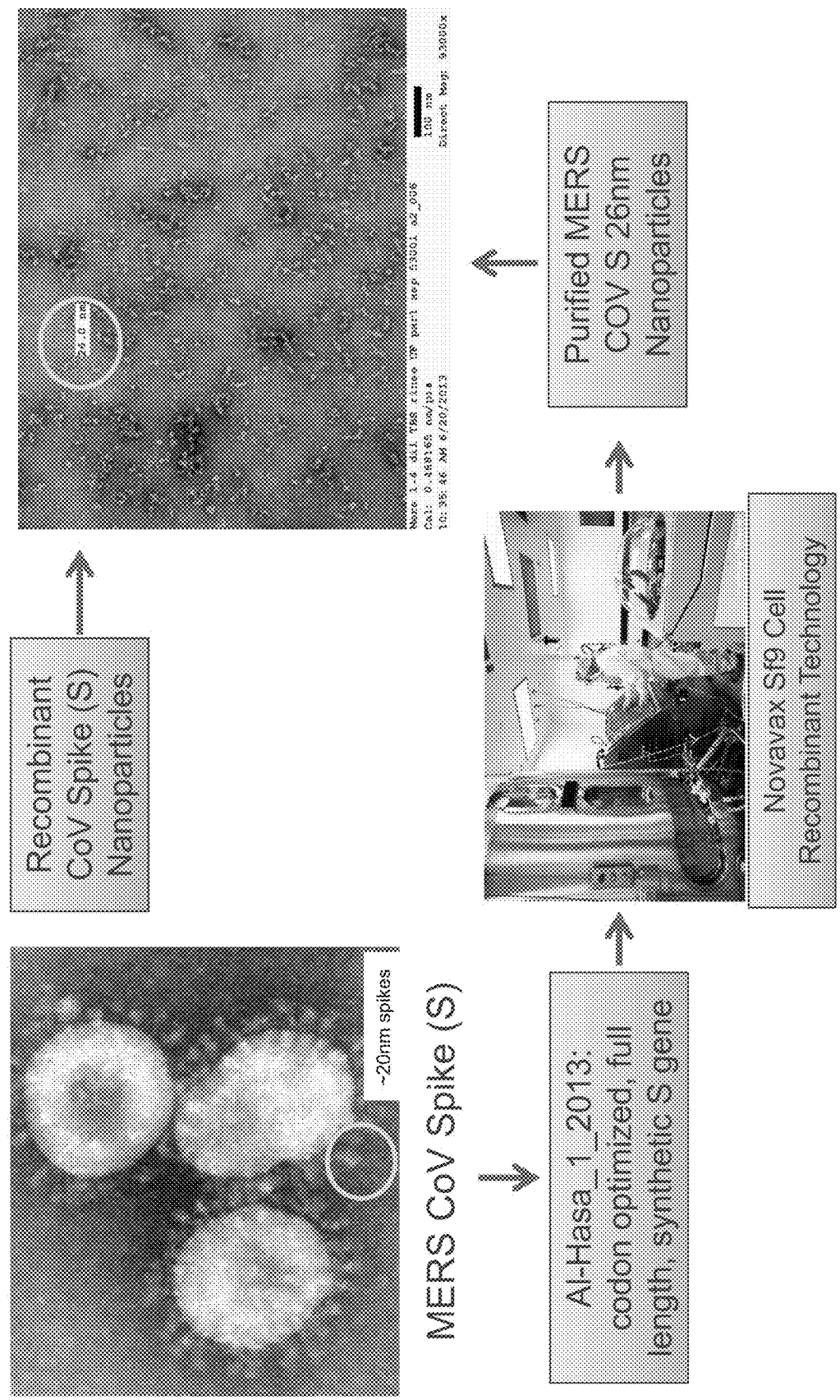
FIG. 2 illustrates vaccine particles obtained by performing methods disclosed herein.

It should be understood that singular forms such as "a," "an," and "the" are used throughout this application for convenience, however, except where context or an explicit statement indicates otherwise, the singular forms are intended to include the plural. Further, it should be understood that every journal article, patent, patent application, publication, and the like that is mentioned herein is hereby incorporated by reference in its entirety and for all purposes. All numerical ranges should be understood to include each and every numerical point within the numerical range, and should be interpreted as reciting each and every numerical point individually. The endpoints of all ranges directed to the same component or property are inclusive, and intended to be independently combinable.

"About" includes all values having substantially the same effect, or providing substantially the same result, as the reference value. Thus, the range encompassed by the term "about" will vary depending on context in which the term is used, for instance the parameter that the reference value is associated with. Thus, depending on context, "about" can mean, for example, ±15%, ±10%, ±5%, ±4%, ±3%, ±2%, ±1%, or ±less than 1%. Importantly, all recitations of a reference value preceded by the term "about" are intended to also be a recitation of the reference value alone.

As used herein, the term "baculovirus," also known as baculoviridae, refers to a family of enveloped DNA viruses of arthropods, members of which may be used as expression vectors for producing recombinant proteins in insert cell cultures. The virion contains one or more rod-shaped nucleocapsids containing a molecule of circular supercoiled double-stranded DNA (Mr $54\times10^6$-$154\times10^6$). The virus used as a vector is generally *Autographa californica* nuclear polyhedrosis virus (NVP). Expression of introduced genes is under the control of the strong promoter that normally regulates expression of the polyhedron protein component of the large nuclear inclusion in which the viruses are embedded in the infected cells.

As used herein, the term "derived from" refers to the origin or source, and may include naturally occurring, recombinant, unpurified, or purified molecules.

As used herein, the term "macromolecular protein structure" refers to the construction or arrangement of one or more proteins.

As used herein, the term "vaccine" refers to a preparation of dead or weakened pathogens, or of derived antigenic determinants that is used to induce formation of antibodies or immunity against the pathogen. A vaccine is given to provide immunity to the disease, for example, MERS which is caused by MERS CoV viruses or SARS, which is caused by SARS CoV viruses. The present disclosure provides vaccine compositions that are immunogenic and provide protection. In addition, the term "vaccine" also refers to a suspension or solution of an immunogen (e.g. nanoparticle VLP) that is administered to a vertebrate to produce protective immunity, i.e., immunity that reduces the severity of disease associated with infection.

As used herein the term "substantial immunity" refers to an immune response in which when nanoparticles are administered to a vertebrate there is an induction of the immune system in said vertebrate which results in the prevention of infection, amelioration of infection or reduction of at least one symptom related to virus infection in said vertebrate.

As used herein the term "adjuvant" refers to a compound that, when used in combination with a specific immunogen (e.g. a nanoparticle VLP) in a formulation, augments or otherwise alters or modifies the resultant immune response. Modification of the immune response includes intensification or broadening the specificity of either or both antibody and cellular immune responses. Modification of the immune response can also mean decreasing or suppressing certain antigen-specific immune responses.

As used herein the term "immune stimulator" refers to a compound that enhances an immune response via the body's own chemical messengers (cytokines). These molecules comprise various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immune stimulator molecules can be administered in the same formulation as the nanoparticle VLPs, or can be administered separately. Either the protein or an expression vector encoding the protein can be administered to produce an immunostimulatory effect.

As used herein an "effective dose" generally refers to that amount of the nanoparticle sufficient to induce immunity, to prevent and/or ameliorate virus infection or to reduce at least one symptom of infection and/or to enhance the efficacy of another dose of a nanoparticle. An effective dose may refer to the amount of the nanoparticle sufficient to delay or minimize the onset of an infection. An effective dose may also refer to the amount of the nanoparticle that provides a therapeutic benefit in the treatment or management of infection. Further, an effective dose is the amount with respect to the nanoparticles alone, or in combination with other therapies, that provides a therapeutic benefit in the treatment or management of a viral infection. An effective dose may also be the amount sufficient to enhance a subject's (e.g., a human's) own immune response against a subsequent exposure to virus. Levels of immunity can be monitored, e.g., by measuring amounts of neutralizing secretory and/or serum antibodies, e.g., by plaque neutralization, complement fixation, enzyme-linked immunosorbent, or microneutralization assay. In the case of a vaccine, an "effective dose" is one that prevents disease or reduces the severity of symptoms.

As used herein the term "substantially protective antibody response" refers to an immune response mediated by antibodies against a virus, which is exhibited by a vertebrate (e.g., a human), that prevents or ameliorates infection or reduces at least one symptom thereof. Nanoparticles can stimulate the production of antibodies that, for example, neutralizing antibodies that block viruses from entering cells, blocks replication of said virus by binding to the virus, and/or protect host cells from infection and destruction.

As used herein the term "substantially protective cellular response" refers to an immune response that is mediated by T-lymphocytes and/or other white blood cells against virus, exhibited by a vertebrate (e.g., a human), that prevents or ameliorates infection or reduces at least one symptom thereof. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

As used herein the term "substantial immunity in a population-wide basis" refers to immunity as a result of nanoparticles administered to individuals in a population. The immunity in said individual in said population results in the prevention, amelioration of infection, or reduction of at least one symptom related to virus infection in said individual, and prevents the spread of said virus to others in the population. The term population is defined as group of individuals (e.g. schoolchildren, elderly, healthy individuals etc.) and may comprise a geographic area (e.g. specific cities, schools, neighborhoods, workplace, country, state, etc.).

As use herein, the term "antigenic formulation" or "antigenic composition" refers to a preparation which, when administered to a vertebrate, especially a mammal, will induce an immune response.

As use herein, the term "vertebrate" or "subject" or "patient" refers to any member of the subphylum cordata, including, without limitation, humans and other primates, including non-human primates such as chimpanzees and other apes and monkey species. Farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like are also non-limiting examples. The terms "mammals" and "animals" are included in this definition. Both adult and newborn individuals are intended to be covered.

Nanoparticle VLPs

One of the goals in vaccine development is the production of vaccines that stimulate the immune system against a pathogen, but are not themselves infectious. This has lead away from the use of whole virions in vaccines toward more minimalist compositions. However, these minimalist compositions present their own obstacles, and in particular often exhibit a decreased immunogenicity requiring the use of adjuvants and systems that boost the immune response. Nanoparticles comprising native viral proteins offer a means of immunization that harnesses the viruses' natural ability to enter the cell and stimulate an immune response.

Nanoparticles, as disclosed herein, are a particular type of virus-like particle (VLP). The nanoparticles contain viral proteins but do not contain any viral genetic material, and thus are not infectious themselves. The nanoparticles are formed by self-assembly of recombinantly-produced viral proteins and stimulate especially useful immune responses. Without being bound by theory, it is though that the size, repetitive structure, and particulate nature contribute to the potent immune responses. Notably, the potent immune response may be obtained even in the absence of an adjuvant.

Nanoparticle Structure

The nanoparticles contain viral proteins, such as viral capsid or coat proteins, arranged in a polymeric form. Typically, the polymer is at least a trimer of viral proteins. In other aspects the polymer may contain more than three monomers of viral proteins. For example, the polymer may contain 4, 5, 6, 7, 8, 9 or 10 monomer units (referred to as a O-mer, 5-mer, 6-mer and so on). In particular aspects, the polymers may be assembled into higher order structures. Thus, for example, the nanoparticles may contain at least about 3 polymers, at least about 5 polymers, at least about 10 polymers, at least about 15 polymers, at least about 20 polymers, or at least about 30 polymers. In particular aspects, the nanoparticle contains between about 5 and 15 polymers, between about 5 and 20 polymers, or between about 5 and 30 polymers. In yet other aspects, the nanoparticle contains between about 5 and 200 polymers, between about 10 and 200 polymers or between about 10 and 50 polymers. Thus, in particular examples, the nanoparticles may contain about 5 to about 20 trimers.

Generally, the more complex higher order structures may be obtained by increasing the protein concentration. In one example, lower protein concentrations yield nanoparticles comprising about 5 polymers, while higher protein concentrations (e.g. 30-50 µg/mL) yield nanoparticles comprising about 10 to 20 polymers. In one non-limiting example, the concentration of the nanoparticles is at least about 10 µg/mL, about 20 µg/mL, about 30 µg/mL, about 40 µg/mL, about 50 µg/mL, about 60 µg/mL, about 100 µg/mL, about 200 µg/mL, or about 500 µg/mL. In particular, the concentration of the nanoparticles may be between about 10 µg/mL to about 1 mg/mL, or between about 20 µg/mL to about 500 µg/mL, or between about 30 µg/mL to about 100 µg/mL, or between about 30 µg/mL to about 50 µg/mL.

Nanoparticle Proteins

The nanoparticles disclosed herein can comprise any MERS-CoV protein, including, but not limited to the Spike (S) protein, the Membrane (M) protein, the Nucelocapsid (N) protein, and Envelope (E) protein, or a combination thereof. The proteins may be obtained or derived from any MERS-CoV strain, clade, or species. The nanoparticles can comprise one or more proteins from one or more MERS-CoV isolates, strains, clades, and/or species. In one embodiment, the proteins are obtained or derived from the Jordan-N3/2012 strain (GenBank KC776174.1) of MERS-CoV. In another embodiment, the proteins are obtained or derived from the Munich_2013 strain of MERS-CoV. In another embodiment, the proteins are obtained or derived from the Al-Hasa_1_2013 strain of MERS-CoV. The proteins comprising the nanoparticles may also be derived or obtained from a variety of other sources, including but not limited to, the Hafr-Al-batin_1_2013 strain, the Bisha_1_2012 strain, the Qatar_3_2013 strain, the Camel_Egypt_2013 strain, MERS-CoV clade A viruses, MERS-CoV clade B viruses, the closely related HKU4 and HKU5 bat coronavirus strains, and/or other closely related coronaviruses. The MERS-CoV proteins may also be produced synthetically or recombinantly in vitro. In one embodiment, the proteins are produced recombinantly in insect cells, such as 519 cells.

In one embodiment, the polymer may comprise one or more different types of MERS-CoV proteins. In a further embodiment, the polymer comprises a single type of MERS-CoV protein. In a preferred embodiment, the polymer comprises Spike protein only. In another embodiment, the protein in a polymer consists of Spike protein. In a further embodiment, the nanoparticle does not contain membrane or nucleocapsid proteins. In another further embodiment, the nanoparticle does not comprise any viral nucleic acid sequences.

In one embodiment, the nanoparticle comprises a Spike protein or a fragment thereof. In another further embodiment, the nanoparticle comprises a trimer of Spike proteins, or fragments thereof. In another embodiment, the nanoparticle comprises at least one polymer of Spike protein encoded by SEQ ID NO: 1. In another embodiment, the nanoparticle comprises at least one polymer of Spike protein comprising SEQ ID NO: 2. In another embodiment, the nanoparticle comprises at least one polymer of Spike protein consisting of SEQ ID NO: 2. In a further embodiment, the nanoparticle comprises at least one polymer of the receptor binding domain (RBD) of the Spike protein.

Nanoparticles may be prepared as described in the art (e.g. as described in US20100239617, published, Sep. 23, 2010 and incorporated herein for all purposes). General texts which describe molecular biological techniques, which are applicable to the present disclosure, such as cloning, mutation, cell culture and the like, include Berger and Kimmel, Guide to Molecular Cloning Techniques, Methods in Enzymology volume 152 Academic Press, Inc., San Diego, Calif. (Berger); Sambrook et al., Molecular Cloning—A Laboratory Manual (3rd Ed.), Vol. 1-3, Cold Spring Harbor Laboratory, Cold Spring Harbor, N.Y., 2000 ("Sambrook") and Current Protocols in Molecular Biology, F. M. Ausubel et al., eds., Current Protocols, a joint venture between Greene Publishing Associates, Inc. and John Wiley & Sons, Inc., ("Ausubel"). These texts describe mutagenesis, the use of vectors, promoters and many other relevant topics related to cloning and mutation of proteins. Thus, the disclosure also encompasses using known methods of protein engineering and recombinant DNA technology to improve or alter the characteristics of the proteins expressed on or in the nanoparticles. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present disclosure. In one embodiment, mutagenesis can be guided by known information of the naturally occurring molecule or altered or mutated naturally occurring molecule, e.g., sequence, sequence comparisons, physical properties, crystal structure or the like.

MERS Spike Proteins

Suitable Spike proteins or fragments thereof are obtained or derived from MERS-CoV isolates, strains, clades, and/or sequences. Alternatively, they can be produced recombinantly or synthetically. For example, a suitable MERS-CoV amino acid sequence is disclosed in Genbank Accession No. AGN70962 (FIG. 9 (SEQ ID NO: 2)). In one embodiment, the Spike protein or fragment thereof is obtained from an Al-Hasa MERS-CoV strain.

The disclosure provides variants of the MERS-CoV proteins. The variants may contain alterations in the amino acid sequences of the constituent proteins. The term "variant" with respect to a polypeptide refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variations can also include amino acid deletion or insertion, or both. Guidance in determining which amino acid residues can be substituted, inserted, or deleted without eliminating biological or immunological activity can be found using computer programs well known in the art, for example, DNASTAR software.

Natural variants can occur due to antigenic drifts. Antigenic drifts are small changes in the viral proteins that happen continually over time. Thus, a person infected with a particular MERS-CoV virus strain develops antibodies against that virus, as newer virus strains appear, the antibodies against the older strains no longer recognize the newer virus and reinfection can occur. These naturally occurring MERS-CoV proteins and RBD variants may be used to produce nanoparticles as described herein.

In some embodiments, mutations containing alterations which produce silent substitutions, additions, or deletions, but do not alter the properties or activities of the encoded protein or how the proteins are made. Nucleotide variants can be produced for a variety of reasons, e.g., to optimize codon expression for a particular host (change codons in the human mRNA to those preferred by insect cells such as Sf9 cells). See U.S. patent publication 2005/0118191, herein incorporated by reference in its entirety for all purposes. In a particular aspect, the preferred protein is encoded by a codon-optimized nucleotide sequence such as shown in FIG. 8 (SEQ ID NO: 1). The nucleic acid and polypeptides may be at least 85%, 90%, 95%, 96%, 97%, 98% or 99% identical to the sequences shown in FIGS. 8 and 9 (SEQ ID NOS: 1 and 2).

In addition, the nucleotides can be sequenced to ensure that the correct coding regions were cloned and do not contain any unwanted mutations. The nucleotides can be subcloned into an expression vector (e.g. baculovirus) for expression in any cell. The above is only one example of how the viral proteins can be cloned. A person with skill in the art understands that additional methods are available and are possible.

This disclosure also provides for constructs and methods that will increase the efficiency of nanoparticle production. For example, removing cleavage sites from proteins in order to increase protein expression. Other methods comprise the addition of leader sequences for more efficient transporting. For example, a heterologous signal sequence can be fused to a MERS protein. In one embodiment, the signal sequence can be derived from the gene of an insect cell. In another embodiment, the signal peptide is the chitinase signal sequence, which works efficiently in baculovirus expression systems. In other embodiment, interchanging leader sequences between proteins can provide better protein transport.

Suitable vectors encoding MERS-CoV proteins or fragments thereof may be used. The vector may be, for example, a phage, plasmid, viral, or retroviral vector. In one embodiment, the vector is a recombinant baculovirus vector. The constructs and/or vectors that encode genes should be operatively linked to an appropriate promoter, such as the AcM-NPV polyhedrin promoter (or other baculovirus), phage lambda PL promoter, the E. coli lac, phoA and tac promoters, the SV40 early and late promoters, and promoters of retroviral LTRs are non-limiting examples. Other suitable promoters will be known to the skilled artisan depending on the host cell and/or the rate of expression desired. The expression constructs will further contain sites for transcription initiation, termination, and, in the transcribed region, a ribosome binding site for translation. The coding portion of the transcripts expressed by the constructs will preferably include a translation initiating codon at the beginning and a termination codon appropriately positioned at the end of the polypeptide to be translated.

The expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Among vectors preferred are virus vectors, such as baculovirus, poxvirus (e.g., vaccinia virus, avipox virus, canarypox virus, fowlpox virus, raccoonpox virus, swinepox virus, etc.), adenovirus (e.g., canine adenovirus), herpesvirus, and retrovirus. Bacterial vectors may also be used. Exemplary bacterial vectors include, pQE70, pQE60 and pQE-9, pBluescript vectors, Phagescript vectors, pNH8A, pNH16a, pNH18A, pNH46A, ptrc99a, pKK223-3, pKK233-3, pDR540, pRIT5. Among preferred eukaryotic vectors are pFastBac1 pWINEO, pSV2CAT, pOG44, pXT1 and pSG, pSVK3, pBPV, pMSG, and pSVL. Other suitable vectors will be readily apparent to the skilled artisan.

Vectors, e.g., vectors comprising MERS-CoV polynucleotides, can be transfected into host cells according to methods well known in the art. For example, introducing nucleic acids into eukaryotic cells can be by calcium phosphate co-precipitation, electroporation, microinjection, lipofection, and transfection employing polyamine transfection reagents. In one embodiment, the said vector is a recombinant baculovirus.

Recombinant vectors such as those disclosed above can be used to transfect, infect, or transform and can express proteins in eukaryotic cells and/or prokaryotic cells. Among eukaryotic host cells are yeast, insect, avian, plant, *C. elegans* (or nematode) and mammalian host cells. Non limiting examples of insect cells are, *Spodoptera frugiperda* (Sf) cells, e.g. Sf9, Sf21, *Trichoplusia ni* cells, e.g. High Five cells, and *Drosophila* S2 cells. Examples of fungi (including yeast) host cells are *S. cerevisiae, Kluyveromyces lactis* (*K. lactis*), species of *Candida* including *C. albicans* and *C. glabrata, Aspergillus nidulans, Schizosaccharomyces pombe* (*S. pombe*), *Pichia pastoris*, and *Yarrowia lipolytica*. Examples of mammalian cells are COS cells, baby hamster kidney cells, mouse L cells, LNCaP cells, Chinese hamster ovary (CHO) cells, human embryonic kidney (HEK) cells, and African green monkey cells, CV1 cells, HeLa cells, MDCK cells, Vero and Hep-2 cells. *Xenopus laevis* oocytes, or other cells of amphibian origin, may also be used. Prokaryotic host cells include bacterial cells, for example, *E. coli, B. subtilis*, and mycobacteria.

Methods to grow cells engineered to produce nanoparticles include, but are not limited to, batch, batch-fed, continuous and perfusion cell culture techniques. Cell culture means the growth and propagation of cells in a bioreactor (a fermentation chamber) where cells propagate and express protein (e.g. recombinant proteins) for purification and isolation. Typically, cell culture is performed under sterile, controlled temperature and atmospheric conditions in a bioreactor. A bioreactor is a chamber used to culture cells in which environmental conditions such as temperature, atmosphere, agitation and/or pH can be monitored. In one embodiment, said bioreactor is a stainless steel chamber. In another embodiment, said bioreactor is a pre-sterilized plastic bag (e.g. Cellbag®, Wave Biotech, Bridgewater, N.J.). In other embodiment, said pre-sterilized plastic bags are about 50 L to 1000 L bags.

The nanoparticles may then be isolated using methods that preserve the integrity thereof, such as by gradient centrifugation, e.g., cesium chloride, sucrose and iodixanol, as well as standard purification techniques including, e.g., ion exchange and gel filtration chromatography.

The following is an example of how nanoparticles can be made, isolated and purified. Usually nanoparticles are produced from recombinant cell lines engineered to create nanoparticles when said cells are grown in cell culture.

For example, production of nanoparticles can start by seeding Sf9 cells (non-infected) into shaker flasks, allowing the cells to expand and scaling up as the cells grow and multiply (for example from a 125-ml flask to a 50 L Wave bag). The medium used to grow the cell is formulated for the appropriate cell line (preferably serum free media, e.g. insect medium ExCell-420, JRH). Next, said cells are infected with recombinant baculovirus at the most efficient multiplicity of infection (e.g. from about 1 to about 3 plaque forming units per cell). Once infection has occurred, the proteins are expressed from the virus genome, self-assemble into nanoparticle VLPs and are secreted from the cells approximately 24 to 72 hours post infection. Usually, infection is most efficient when the cells are in mid-log phase of growth ($4-8 \times 10^6$ cells/ml) and are at least about 90% viable.

Alternatively, nanoparticles may be produced, for example, by infecting host cells (e.g. Sf9) cells with a recombinant baculovirus comprising nucleotide sequences encoding the MERS-CoV protein or proteins or interest. The infected cells are incubated and harvested. The MERS-CoV protein (e.g. Spike protein) is extracted from the cellular membrane with a detergent. The proteins are then allowed to naturally assemble to form structures (e.g. trimers) which are then purified. The removal of the detergent during purification allows the proteins to form higher order structures such as nanoparticles comprising multiple structures (e.g. protein-protein micellular nanoparticles comprising protein trimers). Generally, the number of structures in the nanoparticles is influenced by the protein concentration, with higher protein concentrations yielding nanoparticles comprising greater numbers of structures (e.g. trimers).

Nanoparticles can be harvested approximately 48 to 96 hours post infection, when the levels of nanoparticle VLPs in the cell culture medium are near the maximum but before extensive cell lysis. The Sf9 cell density and viability at the time of harvest can be about $0.5 \times 10^6$ cells/ml to about $1.5 \times 10^6$ cells/ml with at least 20% viability, as shown by dye exclusion assay. Next, the medium is removed and clarified. NaCl can be added to the medium to a concentration of about 0.4 to about 1.0 M, preferably to about 0.5 M, to avoid undesirable aggregation. The removal of cell and cellular debris from the cell culture medium containing nanoparticles can be accomplished by tangential flow filtration (TFF) with a single use, pre-sterilized hollow fiber 0.5 or 1.00 μm filter cartridge or a similar device.

Next, nanoparticles in the clarified culture medium can be concentrated by ultrafiltration using a disposable, pre-sterilized 500,000 molecular weight cut off hollow fiber cartridge. The concentrated nanoparticles can be diafiltrated against 10 volumes pH 7.0 to 8.0 phosphate-buffered saline (PBS) containing 0.5 M NaCl to remove residual medium components.

The concentrated, diafiltered nanoparticles can be furthered purified on a 20% to 60% discontinuous sucrose gradient in pH 7.2 PBS buffer with 0.5 M NaCl by centrifugation at 6,500×g for 18 hours at about 4° C. to about 10° C. Usually nanoparticle VLPs will form a distinctive visible band between about 30% to about 40% sucrose or at the interface (in a 20% and 60% step gradient) that can be collected from the gradient and stored. This product can be diluted to comprise 200 mM of NaCl in preparation for the next step in the purification process. This product contains nanoparticle VLPs and may contain intact baculovirus particles.

Further purification of nanoparticles can be achieved by anion exchange chromatography, or 44% isopycnic sucrose cushion centrifugation. In anion exchange chromatography, the sample from the sucrose gradient (see above) is loaded into column containing a medium with an anion (e.g. Matrix Fractogel EMD TMAE) and eluded via a salt gradient (from about 0.2 M to about 1.0 M of NaCl) that can separate the nanoparticle from other contaminates (e.g. baculovirus and DNA/RNA). In the sucrose cushion method, the sample comprising the nanoparticles is added to a 44% sucrose cushion and centrifuged for about 18 hours at 30,000 g. Nanoparticles form a band at the top of 44% sucrose, while baculovirus precipitates at the bottom and other contaminating proteins stay in the 0% sucrose layer at the top. The nanoparticle peak or band is collected.

The intact baculovirus can be inactivated, if desired. Inactivation can be accomplished by chemical methods, for example, formalin or β-propyl lactone (BPL). Removal and/or inactivation of intact baculovirus can also be largely accomplished by using selective precipitation and chromatographic methods known in the art, as exemplified above. Methods of inactivation comprise incubating the sample containing the nanoparticles in 0.2% of BPL for 3 hours at about 25° C. to about 27° C. The baculovirus can also be inactivated by incubating the sample containing the nanoparticles at 0.05% BPL at 4° C. for 3 days, then at 37° C. for one hour.

After the inactivation/removal step, the product comprising the nanoparticles can be run through another diafiltration step to remove any reagent from the inactivation step and/or any residual sucrose, and to place the nanoparticles into the desired buffer (e.g. PBS). The solution comprising nanoparticles can be sterilized by methods known in the art (e.g. sterile filtration) and stored in the refrigerator or freezer.

The above techniques can be practiced across a variety of scales. For example, T-flasks, shake-flasks, spinner bottles, up to industrial sized bioreactors. The bioreactors can comprise either a stainless steel tank or a pre-sterilized plastic bag (for example, the system sold by Wave Biotech, Bridgewater, N.J.). A person with skill in the art will know what is most desirable for their purposes.

Pharmaceutical or Vaccine Formulations and Administration

The pharmaceutical compositions useful herein contain a pharmaceutically acceptable carrier, including any suitable diluent or excipient, which includes any pharmaceutical agent that does not itself induce the production of an immune response harmful to the vertebrate receiving the composition, and which may be administered without undue toxicity along with a nanoparticle. As used herein, the term "pharmaceutically acceptable" means being approved by a regulatory agency of the Federal or a state government or listed in the U.S. Pharmacopia, European Pharmacopia or other generally recognized pharmacopia for use in vertebrates, and more particularly in humans.

Generally, the nanoparticles are administered in an effective amount or quantity (as defined above) sufficient to stimulate an immune response against one or more strains of MERS CoV virus. These compositions may be used as a vaccine and/or antigenic compositions for inducing a protective immune response in a vertebrate. The compositions may contain nanoparticles having different polymer types. For example, the compositions may contain primarily trimers, with the remainder being composed of different polymers. In one embodiment, the nanoparticles administered in an effective amount to stimulate an immune response against one or more strains of MERS-CoV virus comprise at least about 5 to 100 trimers, at least about 10 to 90 trimers, at least about 20 to 50 trimers, at least about 10 to 30 trimers, or at least about 10 to 20 trimers of MERS-CoV proteins. In a further composition embodiment, the nanoparticles administered comprise at least about 5 to 100 trimers, at least about 10 to 90 trimers, at least about 20 to 50 trimers, at least about 10 to 30 trimers, or at least about 10 to 20 trimers of Spike protein or a fragment thereof (such as RBD).

In one non-limiting embodiment, the concentration of the nanoparticles is at least about 10 µg/mL, about 20 µg/mL, about 30 µg/mL, about 40 µg/mL, about 50 µg/mL, about 60 µg/mL, about 100 µg/mL, about 200 µg/mL, or about 500 µg/mL. In particular aspects, the concentration of the nanoparticles is between about 10 µg/mL to about 1 mg/mL, or between about 20 µg/mL to about 500 µg/mL, or between about 30 µg/mL to about 100 µg/mL, or between about 30 µg/mL to about 50 µg/mL.

In other examples, the compositions may contain higher order nanoparticles such as 5-mers to 6-mers. In particular aspects, the compositions contain at least 70% 5-mers to ti-mers, at least 80% 5-mers to 6-mers, or at least 90% 5-mers to 6-mers. In other aspects, the composition contains at least 70% 5-mers to 6-mers, at least 80% 5-mers to 6-mers, or at least 90% 5-mers to 6-mers.

In one embodiment, pharmaceutical formulations disclosed herein comprise nanoparticles comprising a MERS-CoV protein, often a Spike protein, and a pharmaceutically acceptable carrier or excipient.

In other embodiments, compositions may contain nanoparticles containing MERS-CoV proteins, or variants such as the RBD variant, from different MERS strains. Such compositions may be administered to provide immunity to multiple, different strains. In an aspect, a composition may contain nanoparticles to provide an immune response against a first strain, second strain, a third strain. In another aspect, the nanoparticles may provide an immune response against four, five or six strains. In another embodiment, the pharmaceutical formulations comprise a purified, high affinity antibody produced in an animal administered with the nanoparticles.

Pharmaceutically acceptable carriers include but are not limited to saline, buffered saline, dextrose, water, glycerol, sterile isotonic aqueous buffer, and combinations thereof. A thorough discussion of pharmaceutically acceptable carriers, diluents, and other excipients is presented in Remington's Pharmaceutical Sciences (Mack Pub. Co. N.J. current edition). The formulation should suit the mode of administration. In a preferred embodiment, the formulation is suitable for administration to humans, preferably is sterile, non-particulate and/or non-pyrogenic.

The composition, if desired, can also contain minor amounts of wetting or emulsifying agents, or pH buffering agents. The composition can be a solid form, such as a lyophilized powder suitable for reconstitution, a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

The disclosure also provides for a pharmaceutical pack or kit comprising one or more containers filled with one or more of the ingredients of the immunogenic vaccine formulations. In a preferred embodiment, the kit comprises two containers, one containing nanoparticles and the other containing an adjuvant. Associated with such container(s) can be a notice in the form prescribed by a governmental agency regulating the manufacture, use or sale of pharmaceuticals or biological products, which notice reflects approval by the agency of manufacture, use or sale for human administration.

Formulations may be packaged in a hermetically sealed container such as an ampoule or sachette indicating the quantity of composition. In one embodiment, the composition is supplied as a liquid, in another embodiment, as a dry sterilized lyophilized powder or water free concentrate in a hermetically sealed container and can be reconstituted, e.g., with water or saline to the appropriate concentration for administration to a subject. Preferably, the composition is supplied as a dry sterile lyophilized powder in a hermetically sealed container at a unit dosage of preferably, about 1 µg, about 5 µg, about 10 µg, about 20 µg, about 25 µg, about 30 µg, about 50 µg, about 100 µg, about 125 µg, about 150 µg, or about 200 µg. Alternatively, the unit dosage of the composition is less than about 1 µg, (for example about 0.08 µg, about 0.04 µg, about 0.2 µg, about 0.4 µg, about 0.8 µg, about 0.5 µg or less, about 0.25 µg or less, or about 0.1 µg or less), or more than about 125 µg, (for example about 150 µg or more, about 250 µg or more, or about 500 µg or more). These doses may be measured as total nanoparticles or as µg of MERS-CoV protein (e.g. Spike protein, or fragment thereof). The nanoparticle composition should be administered within about 12 hours, preferably within about 6 hours, within about 5 hours, within about 3 hours, or within about 1 hour after being reconstituted from the lyophilized powder.

In an alternative embodiment, a nanoparticle composition is supplied in liquid form in a hermetically sealed container indicating the quantity and concentration of the nanoparticle composition. Preferably, the liquid form of the nanoparticle composition is supplied in a hermetically sealed container at least about 50 µg/ml, more preferably at least about 100 µg/ml, at least about 200 µg/ml, at least 500 µg/ml, or at least 1 mg/ml.

The nanoparticles may be administered to an animal to elicit an immune response against MERS-CoV. In one embodiment, the animal is susceptible to MERS-CoV infection. In one embodiment, the animal is a human. Preferably, administration of the nanoparticles elicits substantial immunity against at least one MERS-CoV strain, isolate, clade, and/or species. In one embodiment, administration of the nanoparticles elicits substantial immunity against at least 2 or more MERS-CoV strains, isolates, clades, and/or species. In a further embodiment, administration of the nanoparticles elicits substantial immunity against another coronavirus. Typically, the dose can be adjusted within this range based on, e.g., age, physical condition, body weight, sex, diet, time of administration, and other clinical factors.

Thus, disclosed herein are methods of formulating a vaccine or antigenic composition that induces substantial immunity to virus infection or at least one symptom thereof to a subject, comprising adding to said formulation an effective dose of a nanoparticle.

While stimulation of substantial immunity with a single dose is preferred, additional dosages can be administered, by the same or different route, to achieve the desired effect. In neonates and infants, for example, multiple administrations may be required to elicit sufficient levels of immunity. Administration can continue at intervals throughout childhood, as necessary to maintain sufficient levels of protection against infection. Similarly, adults who are particularly susceptible to repeated or serious infection, such as, for example, health care workers, day care workers, family members of young children, the elderly, and individuals with compromised cardiopulmonary function may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

Thus, in one embodiment, a method to induce substantial immunity to virus infection or at least one symptom thereof in a subject, comprises administering at least one effective dose of a nanoparticle, wherein the nanoparticle comprises at least one trimer comprising MERS CoV Spike protein or fragment thereof. In other aspects the nanoparticle comprises at least one trimer consisting essentially of a MERS CoV Spike protein or a fragment thereof. Indeed, the Spike protein may be the only protein in the trimer and/or nanoparticle.

Methods of administering a composition comprising nanoparticles (vaccine and/or antigenic formulations) include, but are not limited to, parenteral administration (e.g., intradermal, intramuscular, intravenous and subcutaneous), epidural, and mucosal (e.g., intranasal and oral or pulmonary routes or by suppositories). In a specific embodiment, compositions of the present disclosure are administered intramuscularly, intravenously, subcutaneously, transdermally or intradermally. The compositions may be administered by any convenient route, for example by infusion or bolus injection, by absorption through epithelial or mucocutaneous linings (e.g., oral mucous, colon, conjunctiva, nasopharynx, oropharynx, vagina, urethra, urinary bladder and intestinal mucosa, etc.) and may be administered together with other biologically active agents. In some embodiments, intranasal or other mucosal routes of administration of a composition comprising nanoparticles may induce an antibody or other immune response that is substantially higher than other routes of administration. In another embodiment, intranasal or other mucosal routes of administration of a composition comprising nanoparticles may induce an antibody or other immune response that will induce cross protection against other strains of viruses. Administration can be systemic or local. The prophylactic vaccine formulation is systemically administered, e.g., by subcutaneous or intramuscular injection using a needle and syringe, or a needle-less injection device. Alternatively, the vaccine formulation is administered intranasally, either by drops, large particle aerosol (greater than about 10 microns), or spray into the upper respiratory tract. While any of the above routes of delivery results in an immune response, intranasal administration confers the added benefit of eliciting mucosal immunity at the site of entry of the virus.

In yet another embodiment, the vaccine and/or antigenic formulation is administered in such a manner as to target mucosal tissues in order to elicit an immune response at the site of immunization. For example, mucosal tissues such as gut associated lymphoid tissue (GALT) can be targeted for immunization by using oral administration of compositions which contain adjuvants with particular mucosal targeting properties. Additional mucosal tissues can also be targeted, such as nasopharyngeal lymphoid tissue (NALT) and bronchial-associated lymphoid tissue (BALT).

Vaccines and/or antigenic formulations may also be administered on a dosage schedule, for example, an initial administration of the vaccine composition with subsequent booster administrations. In particular embodiments, a second dose of the composition is administered anywhere from two weeks to one year, preferably from about 1, about 2, about 3, about 4, about 5 to about 6 months, after the initial administration. Additionally, a third dose may be administered after the second dose and from about three months to about two years, or even longer, preferably about 4, about 5, or about 6 months, or about 7 months to about one year after the initial administration. The third dose may be optionally administered when no or low levels of specific immunoglobulins are detected in the serum and/or urine or mucosal secretions of the subject after the second dose. In a preferred embodiment, a second dose is administered about one month after the first administration and a third dose is administered about six months after the first administration. In another embodiment, the second dose is administered about six months after the first administration.

In another embodiment, a nanoparticle may be administered as part of a combination therapy. For example, nanoparticles may be formulated with other immunogenic compositions and/or antivirals.

The dosage of the pharmaceutical formulation can be determined readily by the skilled artisan, for example, by first identifying doses effective to elicit a prophylactic or therapeutic immune response, e.g., by measuring the serum titer of virus specific immunoglobulins or by measuring the inhibitory ratio of antibodies in serum samples, or urine samples, or mucosal secretions. Said dosages can be determined from animal studies.

In addition, human clinical studies can be performed to determine the preferred effective dose for humans by a skilled artisan. Such clinical studies are routine and well known in the art. The precise dose to be employed will also depend on the route of administration. Effective doses may be extrapolated from dose-response curves derived from in vitro or animal test systems.

As also well known in the art, the immunogenicity of a particular composition can be enhanced by the use of non-specific stimulators of the immune response, known as adjuvants. Adjuvants have been used experimentally to promote a generalized increase in immunity against unknown antigens (e.g., U.S. Pat. No. 4,877,611). Immunization protocols have used adjuvants to stimulate responses for many years, and as such, adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation. Adjuvants may be included. Suitable adjuvants include those described in Vogel et al., "A Compendium of Vaccine Adjuvants and Excipients ($2^{nd}$ Edition)," herein incorporated by reference in its entirety for all purposes.

Other exemplary adjuvants include complete Freund's adjuvant (a non-specific stimulator of the immune response containing killed *Mycobacterium tuberculosis*), incomplete Freund's adjuvants and aluminum hydroxide adjuvant. Other adjuvants comprise GMCSP, BCG, aluminum hydroxide, MDP compounds, such as thur-MDP and nor-MDP, CGP (MTP-PE), lipid A, Montanide ISA 206, and monophosphoryl lipid A (MPL). which contains three components extracted from bacteria, MPL, trehalose dimycolate (TDM) and cell wall skeleton (CWS) in a 2% squalene/Tween 80 emulsion also is contemplated. MF-59, Novasomes®, MHC antigens may also be used.

In an embodiment, the adjuvant is a paucilamellar lipid vesicle having about two to ten bilayers arranged in the form of substantially spherical shells separated by aqueous layers surrounding a large amorphous central cavity free of lipid bilayers. Paucilamellar lipid vesicles may act to stimulate the immune response several ways, as non-specific stimulators, as carriers for the antigen, as carriers of additional adjuvants, and combinations thereof. Paucilamellar lipid vesicles act as non-specific immune stimulators when, for example, a vaccine is prepared by intermixing the antigen with the preformed vesicles such that the antigen remains extracellular to the vesicles. By encapsulating an antigen within the central cavity of the vesicle, the vesicle acts both as an immune stimulator and a carrier for the antigen. In another embodiment, the vesicles are primarily made of nonphospholipid vesicles. In other embodiment, the vesicles are Novasomes. Novasomes® are paucilamellar nonphospholipid vesicles ranging from about 100 nm to about 500 nm. They comprise Brij 72, cholesterol, oleic acid and squalene. Novasomes have been shown to be an effective adjuvant for antigens (see, U.S. Pat. Nos. 5,629,021, 6,387,373, and 4,911,928, herein incorporated by reference in their entireties for all purposes).

In one aspect, an adjuvant effect is achieved by use of an agent, such as alum, used in about 0.05 to about 0.1% solution in phosphate buffered saline. Alternatively, the nanoparticles can be made as an admixture with synthetic polymers of sugars (Carbopol) used as an about 0.25% solution. Some adjuvants, for example, certain organic molecules obtained from bacteria; act on the host rather than on the antigen. An example is muramyl dipeptide (N-acetyl-muramyl-L-alanyl-D-isoglutamine [MDP]), a bacterial peptidoglycan. In other embodiments, hemocyanins and hemoerythrins may also be used. The use of hemocyanin from keyhole limpet (KLH) is preferred in certain embodiments, although other molluscan and arthropod hemocyanins and hemoerythrins may be employed.

Various polysaccharide adjuvants may also be used. For example, the use of various pneumococcal polysaccharide adjuvants on the antibody responses of mice has been described (Yin et al., 1989). The doses that produce optimal responses, or that otherwise do not produce suppression, should be employed as indicated (Yin et al., 1989). Polyamine varieties of polysaccharides are particularly preferred, such as chitin and chitosan, including deacetylated chitin. In another embodiment, a lipophilic disaccharide-tripeptide derivative of muramyl dipeptide which is described for use in artificial liposomes formed from phosphatidyl choline and phosphatidyl glycerol.

Other suitable adjuvants include amphipathic and surface active agents, e.g., saponin and derivatives such as QS21 (Cambridge Biotech). Saponin-based adjuvants include those containing Matrix A and Matrix C, alone and in combination. Exemplary suitable saponin-based adjuvants are described in U.S. Published Application, 20120107353 and 20110081378 which are herein incorporated by reference for all purposes.

Nonionic block copolymer surfactants (Rabinovich et al., 1994) may also be employed. Oligonucleotides are another useful group of adjuvants (Yamamoto et al., 1988). Quil A and lentinen are other adjuvants that may be used in certain embodiments.

Another group of adjuvants are the detoxified endotoxins, such as the refined detoxified endotoxin of U.S. Pat. No. 4,866,034. These refined detoxified endotoxins are effective in producing adjuvant responses in vertebrates. Of course, the detoxified endotoxins may be combined with other adjuvants to prepare multi-adjuvant formulation. For example, combination of detoxified endotoxins with trehalose dimycolate is particularly contemplated, as described in U.S. Pat. No. 4,435,386. Combinations of detoxified endotoxins with trehalose dimycolate and endotoxic glycolipids is also contemplated (U.S. Pat. No. 4,505,899), as is combination of detoxified endotoxins with cell wall skeleton (CWS) or CWS and trehalose dimycolate, as described in U.S. Pat. Nos. 4,436,727, 4,436,728 and 4,505,900. Combinations of just CWS and trehalose dimycolate, without detoxified endotoxins, is also envisioned to be useful, as described in U.S. Pat. No. 4,520,019.

Those of skill in the art will know the different kinds of adjuvants that can be conjugated to vaccines, including alkyl lysophosphilipids (ALP); BCG; and biotin (including biotinylated derivatives) among others. Certain adjuvants particularly contemplated for use are the teichoic acids from Gram-cells. These include the lipoteichoic acids (LTA), ribitol teichoic acids (RTA) and glycerol teichoic acid (GTA). Active forms of their synthetic counterparts may also be employed. (Takada et al., 1995).

Various adjuvants, even those that are not commonly used in humans, may still be employed in other vertebrates, where, for example, one desires to raise antibodies or to subsequently obtain activated T cells. The toxicity or other adverse effects that may result from either the adjuvant or the cells, e.g., as may occur using non-irradiated tumor cells, is irrelevant in such circumstances.

Another method of inducing an immune response can be accomplished by formulating the nanoparticles with "immune stimulators." These are the body's own chemical messengers (cytokines) to increase the immune system's response. Immune stimulators include, but not limited to, various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immunostimulatory molecules can be administered in the same formulation as the nanoparticles, or can be administered separately. Either the protein or an expression vector encoding the protein can be administered to produce an immunostimulatory effect.

Alum may be present in a range with a lower limit of: about 0.2 µg, about 0.4 µg, about 0.6 µg about 0.8 µg, about 1 µg, about 2 µg, about 3 µg, about 4 µg, about 5 µg, about 6 µg, about 7 µg, about 9 µg, about 10 µg, about 15 µg, about 20 µg, about 25 µg, about 30 µg, about 35 µg, 40 µg, about 45 µg, about 50 µg, about 60 µg, about 70 µg, about 80 µg, about 90 µg, about 100 µg, about 110 µg, about 120 µg, about 130 µg, about 140 µg, or about 150 µg. Alum may be present at a range with an upper limit of: about 10 µg, about 15 µg, about 20 µg, about 25 µg, about 30 µg, about 35 µg, 40 µg, about 45 µg, about 50 µg, about 60 µg, about 70 µg, about 80 µg, about 90 µg, about 100 µg, about 110 µg, about 120 µg, about 130 µg, about 140 µg, about 150 µg, or about 200 µg. In particular aspects, the alum range is about 80 µg to about 120 µg or about 100 µg to about 120 µg.

The saponin-based adjuvant may be present in a range with a lower limit of: about 0.2 µg, about 0.4 µg, about 0.6

μg about 0.8 μg, about 1 μg, about 2 μg, about 3 μg, about 4 μg, about 5 μg, about 6 μg, about 7 μg, about 9 μg, about 10 μg, about 15 μg, about 20 μg, about 25 μg, or about 30 μg. The saponin-based adjuvant may be present at a range with an upper limit of: about 10 μg, about 15 μg, about 20 μg, about 25 μg, about 30 μg, about 35 μg, 40 μg, about 45 μg, about 50 μg, about 60 μg, about 70 μg, about 80 μg, about 90 μg, about 100 μg, about 110 μg, about 120 μg, about 130 μg, about 140 μg, about 150 μg, or about 200 μg. In particular aspects, the saponin-based adjuvant range is about 5 μg to about 20 μg or about 1 μg to about 10 μg.

These doses are particularly suitable in mice and may be adjusted for human use based on typical mouse weight of 20 g versus human weight of about 60 Kg.

Method of Stimulating an Anti-MERS CoV Immune Response

The nanoparticles are useful for preparing immunogenic compositions to stimulate an immune response that confers immunity or substantial immunity to MERS CoV viruses. Both mucosal and cellular immunity may contribute to immunity to infection and disease. Antibodies secreted locally in the upper respiratory tract are a major factor in resistance to natural infection. Secretory immunoglobulin A (sIgA) is involved in protection of the upper respiratory tract and serum IgG in protection of the lower respiratory tract. The immune response induced by an infection protects against reinfection with the same virus or an antigenically similar viral strain. The antibodies produced in a host after immunization with the nanoparticles disclosed herein can also be administered to others, thereby providing passive administration in the subject.

The present disclosure provides a method of producing high affinity anti-MERS-CoV antibodies. The high affinity antibodies produced by immunization with the nanoparticles disclosed herein are produced by administering an immunogenic composition comprising a MERS-CoV nanoparticle to an animal, collecting the serum and/or plasma from the animal, and purifying the antibody from the serum/and or plasma. In one embodiment, the animal is a human. In one embodiment, the animal is bovine or equine. In another embodiment, the bovine or equine animal is transgenic. In yet a further embodiment, the transgenic bovine or equine animal produces human antibodies. In one embodiment, the method further comprises administration of an adjuvant or immune stimulating compound. In a further embodiment, the purified high affinity antibody is administered to a human subject. In one embodiment, the human subject is at risk of MERS-CoV infection.

Nanoparticles can induce substantial immunity in a vertebrate (e.g. a human) when administered to said vertebrate. The substantial immunity results from an immune response against the nanoparticles that protects or ameliorates infection or at least reduces a symptom of virus infection in said vertebrate. In some instances, if the said vertebrate is infected, said infection will be asymptomatic. The response may be not a fully protective response. In this case, if said vertebrate is infected with a MERS CoV virus, the vertebrate will experience reduced symptoms or a shorter duration of symptoms compared to a non-immunized vertebrate.

In one embodiment, the disclosure provides methods of inducing substantial immunity to virus infection or at least one symptom thereof in a subject, comprising administering at least one effective dose of a nanoparticle. In another embodiment, said induction of substantial immunity reduces duration of MERS symptoms. In another embodiment, a method to induce substantial immunity to virus infection or at least one symptom thereof in a subject, comprises administering at least one effective dose of a nanoparticle. In another embodiment, said subject is a mammal. In another embodiment, said mammal is a human. In a further embodiment, said nanoparticle is formulated with an adjuvant or immune stimulator.

In embodiments, the dose of each antigen present in a composition may be about 0.2 μg, about 0.4 μg, about 0.6 μg about 0.8 μg, about 1 μg, about 2 μg, about 3 μg, about 4 μg, about 5 μg, about 6 μg, about 7 μg, about 9 μg, about 10 μg, about 15 μg, about 20 μg, about 25 μg, about 30 μg, about 35 μg, 40 μg, about 45 μg, about 50 μg, about 60 μg, about 70 μg, about 80 μg, about 90 μg, about 100 μg, about 110 μg, about 120 μg, about 130 μg, about 140 μg, or about 150 μg. For example, amounts can be measured according to MERS Spike protein content. For example, 1 μg of a nanoparticle is about 1 μg of MERS Spike protein.

Antibodies Produced by Immunization with Nanoparticles

The nanoparticles disclosed herein induce the production of high affinity anti-MERS-CoV antibodies in the host. These high affinity anti-MERS-CoV antibodies demonstrate higher affinities than anti-MERS-Co-V antibodies produced through conventional methods (e.g. phage-display; see Zhang et al. 2014)).

The term "affinity" refers to the strength of the interaction between an epitope and an antibody's antigen binding site. The affinity can be determined, for example, using the equation $$K_A = \frac{[Ab-Ag]}{[Ab][Ag]}$$

Where $K_A$=affinity constant; [Ab]=molar concentration of unoccupied binding sites on the antibody; [Ag]=molar concentration of unoccupied binding sites on the antigen; and [Ab-Ag]=molar concentration of the antibody-antigen complex. The $K_A$ describes how much antibody-antigen complex exists at the point when equilibrium is reached. The time taken for this to occur depends on rate of diffusion and is similar for every antibody. However, high-affinity antibodies will bind a greater amount of antigen in a shorter period of time than low-affinity antibodies. The $K_A$ (affinity constant) of the antibodies produced can vary, and range from between about $10^5$ mol$^{-1}$ to about $10^{12}$ mol$^{-1}$ or more. The $K_A$ can be influenced by factors including pH, temperature, and buffer composition.

The antibodies produced can be polyclonal antibodies or monoclonal antibodies. The affinity of monoclonal antibodies can be measured accurately because they are homogeneous and selective for a single epitope. Polyclonal antibodies are heterogeneous and will contain a mixture of antibodies of different affinities recognizing several epitopes—therefore only an average affinity can be determined.

The antibody affinity can be measured using any means commonly employed in the art, including but not limited to the use of biosensors, such as surface plasmon resonance (e.g. Biacore). Resonance units are proportional to the degree of binding of soluble ligand to the immobilized receptor (or soluble antibody to immobilized antigen). Determining the amount of binding at equilibrium with different known concentrations of receptor (antibody) and ligand (protein antigen) allows the calculation of equilibrium constants ($K_A$, $K_D$), and the rates of dissociation and association (koff, kon).

For example, $K_D$ (the equilibrium dissociation constant) is a ratio of koff/kon, between the antibody and its antigen. $K_D$ and affinity are inversely related. The lower the $K_D$ value (lower antibody concentration), the higher the affinity of the antibody. Most antibodies have $K_D$ values in the low micromolar ($10^{-6}$) to nanomolar ($10^{-7}$ to $10^{-9}$) range. High affinity antibodies are generally considered to be in the low nanomolar range ($10^{-9}$) with very high affinity antibodies being in the picomolar ($10^{12}$) range or lower (e.g. $10^{-13}$ to $10^{-14}$ range). In one embodiment, the antibodies produced by immunization with the nanoparticles disclosed herein have a $K_D$ ranging from about $10^{-6}$ to about $10^{-15}$, from about $10^{-7}$ to about $10^{-15}$, from about $10^{-8}$ to about $10^{-15}$, and from about $10^{-9}$ to about $10^{-15}$, from about $10^{-10}$ to about $10^{-15}$, about $10^{-11}$ to about $10^{-15}$, about $10^{-12}$ to about $10^{-15}$, about $10^{-13}$ to about $10^{-14}$, about $10^{-13}$ to about $10^{-15}$, and about $10^{-14}$ to about $10^{-15}$. In a preferred embodiment, the antibodies produced by immunization with the nanoparticles disclosed herein have a $K_D$ ranging from about $10^{-10}$ to about $10^{-14}$.

The antibodies produced by immunization with the nanoparticles disclosed herein have low rate of dissociation ($K_{off}$), indicating they bind tightly to the antigen. In one embodiment, the antibodies produced by immunization with the nanoparticles disclosed herein have a $K_{off}$ ranging from about $10^{-3}$ $M^{-1}$ to about $10^{-13}$ $M^{-1}$, from about $10^{-5}$ $M^{-1}$ to about $10^{-13}$ $M^{-1}$, from about $10^{-6}$ $M^{-1}$ to about $10^{-13}$ $M^{-1}$, from about $10^{-7}$ $M^{-1}$ to about $10^{-13}$ $M^{-1}$, from about $10^{-8}$ $M^{-1}$ to about $10^{-13}$ $M^{-1}$, from about $10^{-9}$ $M^{-1}$ to about $10^{-13}$ $M^{-1}$, from about $10^{-10}$ $M^{-1}$ to about $10^{-13}$ $M^{-1}$, from about $10^{-11}$ $M^{-1}$ to about $10^{-13}$ $M^{-1}$, or from about $10^{-12}$ $M^{-1}$ to about $10^{-13}$ $M^{-1}$. In another embodiment, the antibodies produced by immunization with the nanoparticles disclosed herein have a $K_{off}$ ranging from about $10^{-4}$ $M^{-1}$ to about $10^{-10}$ $M^{-1}$, from about $10^{-4}$ $M^{-1}$ to about $10^{-9}$ $M^{-1}$, or from about $10^{-4}$ $M^{-1}$ to about $10^{-8}$ $M^{-1}$.

The antibodies produced by immunization with the nanoparticles disclosed herein have a high rate of association ($K_{on}$) indicating they bind tightly to the antigen. In one embodiment, the antibodies produced by immunization with the nanoparticles disclosed herein have a $K_{on}$ ranging from about $10^3$ M to about $10^8$ M, from about $10^4$ M to about $10^7$ M, from about $10^4$ M to about $10^6$ M, from about $10^4$ M to about $10^5$ M, from about $10^5$ M to about $10^7$ M, or from about $10^5$ M to about $10^6$ M.

The antibodies produced by immunization with the nanoparticles disclosed herein neutralize the MERS-CoV virus. The antibodies can be broadly neutralizing antibodies and neutralize one or more MERS-CoV virus strains, clades, or coronaviruses, or the antibodies can neutralize only one MERS-CoV virus strain. The neutralization ability of the antibodies can be measured by any means commonly employed in the art, including, but not limited to, Fluorescence Reduction Neutralization Test ($FRNT_{50}$), in vitro cell-based assays which measure the amount of virion released from immunized cells, and in vivo assays which measure the infection in an immunized animal.

This disclosure is further illustrated by the following examples which should not be construed as limiting. The contents of all references, patents and published patent applications cited throughout this application, as well as the Figures, are incorporated by reference in their entirety for all purposes.

EXAMPLE 1

Production of MERS CoV Spike Nanoparticles

The nanoparticles are produced by over-expressing the MERS CoV Spike protein (FIGS. 8 and 9) in baculovirus in Sf9 cells. Following purification the nanoparticle VLPs containing Spike protein was recovered predominantly in trimer form (FIGS. 4 and 6).

EXAMPLE 2

Induction of Immune Response Using MERS CoV Spike Nanoparticles

The VLPs were administered to mice as shown in FIG. 5. At the end of the 45 day period, blood was extracted from the mice to assess the immune response. FIG. 7 illustrates neutralizing antibody titres for mice administered either the SARS CoV Spike nanoparticle VLP or the MERS CoV Spike nanoparticle VLP. The highest response was obtained by using the adjuvant Matrix M1.

EXAMPLE 3

Potent Anti-MERS-CoV Human Immunoglobulin Produced from Transchromosomic Bovines Inhibits MERS-CoV In Vivo To demonstrate that anti-MERS CoV hIgG antibodies and immunoglobulin obtained from Tc bovines after vaccination could neutralize MERS CoV in vitro and in vivo we administered three experimental MERS CoV vaccines to three separate groups of Tc Bovines to induce high titer neutralizing antibodies to MERS CoV. The first vaccine tested was a whole killed Jordan strain (clade A) MERS-CoV virion (WKV) vaccine, the second was an Al-Hasa (clade B) MERS-CoV Spike nanoparticle (SN) vaccine, and the third was an Al-Hasa MERS-CoV Spike protein pDNA vaccine. The pDNA vaccine was found to be poorly immunogenic by in vitro assay and was not evaluated further (data not presented). However convalescent serum and highly purified hIgG immunoglobulin from both the WKV (termed SAB-300) and SN (termed SAB-301) vaccinated Tc bovines were able to cross neutralize virus in vitro, do not induce antibody dependent entry of MERS-CoV into human Raji B cells, and rapidly reduce viral infection (Erasmus strain) in a Ad5-hDPP4 transduced mouse model of MERS-CoV.

Methods and Materials

Animal Studies

Transcromosomic (Tc) Bovine Cloning and Antibody Production

Tc bovines were produced as described in Matsushita, et al. PLoS One, 2014. 9(3): p. e90383, Sano, et al. PLoS One, 2013. 8(10): p. e78119, and Kuroiwa, et al., Nat Biotechnol, 2009. 27(2): p. 173-81. Briefly, the Tc bovines used in this study are homozygous for triple knock-outs in the endogenous bovine immunoglobulin genes (IGHM$^{-/-}$ IGHML1$^{-/-}$ IGL$^{-/-}$) and carry a human artificial chromosome (HAC) consisting of a human chromosome 14 fragment, which contains the entire human immunoglobulin heavy chain locus, and a human chromosome 2 fragment, which contains the entire human immunoglobulin kappa light chain locus.

Inactivated Whole Virion Production

Whole inactivated MERS-CoV virions were produced for vaccination by collecting media from Vero CCL-81 cells infected with the Jordan-N3/2012 strain (GenBank KC776174.1). $4 \times 10^8$ PFU of MERS-CoV was irradiated with a cobalt source until a dose of 6MRads was achieved. The material was safety tested for inactivation. No MERS-CoV specific signal was detected in the irradiated passaged material.

MERS-CoV Spike Nanoparticle Production

Purified Al-Hasa strain MERS-CoV spike protein nanoparticles were produced as described in Coleman et al. 2014. Briefly Sf9 cells at 2-3×10$^6$ cells/ml were infected with specific recombinant baculovirus. Infected Sf9 cells were incubated with continuous agitation at 27±2° C. and harvested at 68-72 hpi by centrifugation at 4000×g for 15 minutes. Spike proteins were extracted from cellular membranes with a non-ionic detergent and insoluble material was removed by centrifugation at 10,000×g for 30 minutes. Spike protein assemblies were purified using a combination of anion exchange, affinity, and size exclusion chromatography. During purification, the majority of the detergent is removed, allowing Spike protein trimers to form higher ordered protein-protein micellular nanoparticles. Purified Spike nanoparticles were 0.2 micron filtered and stored at −80° C.

Tc Bovine Vaccination

As shown in FIG. 10A, three Tc bovines in Group 1 (#2244; #2252 & #2254) were immunized with whole killed MERS-CoV virus (WKV) at 1-2×10$^8$ PPF/dose formulated with Montanide ISA 25 adjuvant (Seppic) as oil-in-water emulsion plus the saponin-derived immune stimulant Quil A (Accurate Chemicals). Two Tc bovines in Group 2 (#2178 & #2183) were immunized with recombinant MERS-CoV Spike Nanoparticle (SN) at 2 mg/dose formulated with Montanide ISA 206 adjuvant as water-in-oil-in-water emulsion plus Quil A. The Tc bovines in both groups were immunized 5 times at three- to four-week intervals.

In Vivo MERS-CoV Challenge Studies in Adenovirus/hDPP4 Mice

Transduced hDPP4 BALB/c mice were infected with the Erasmus strain MERS-CoV. Briefly, BALB/c were injected intraperitoneally with 100 or 500 μg of negative control or test immunoglobulin collected from the bovines (SAB-300 or SAB-301). Twelve hours later, mice were infected intranasally with MERS-CoV (1×10$^5$ PFU) in a total volume of 50 μl. To obtain virus titers, lungs were removed into PBS and homogenized using a manual homogenizer. Virus was titered on Vero 81 cells. Viral titers are expressed as PFU/g tissue for MERS-CoV.

Results and Discussion

Evaluation of Antigen-Specific hIgG Produced in Tc Animals

Figure 10:
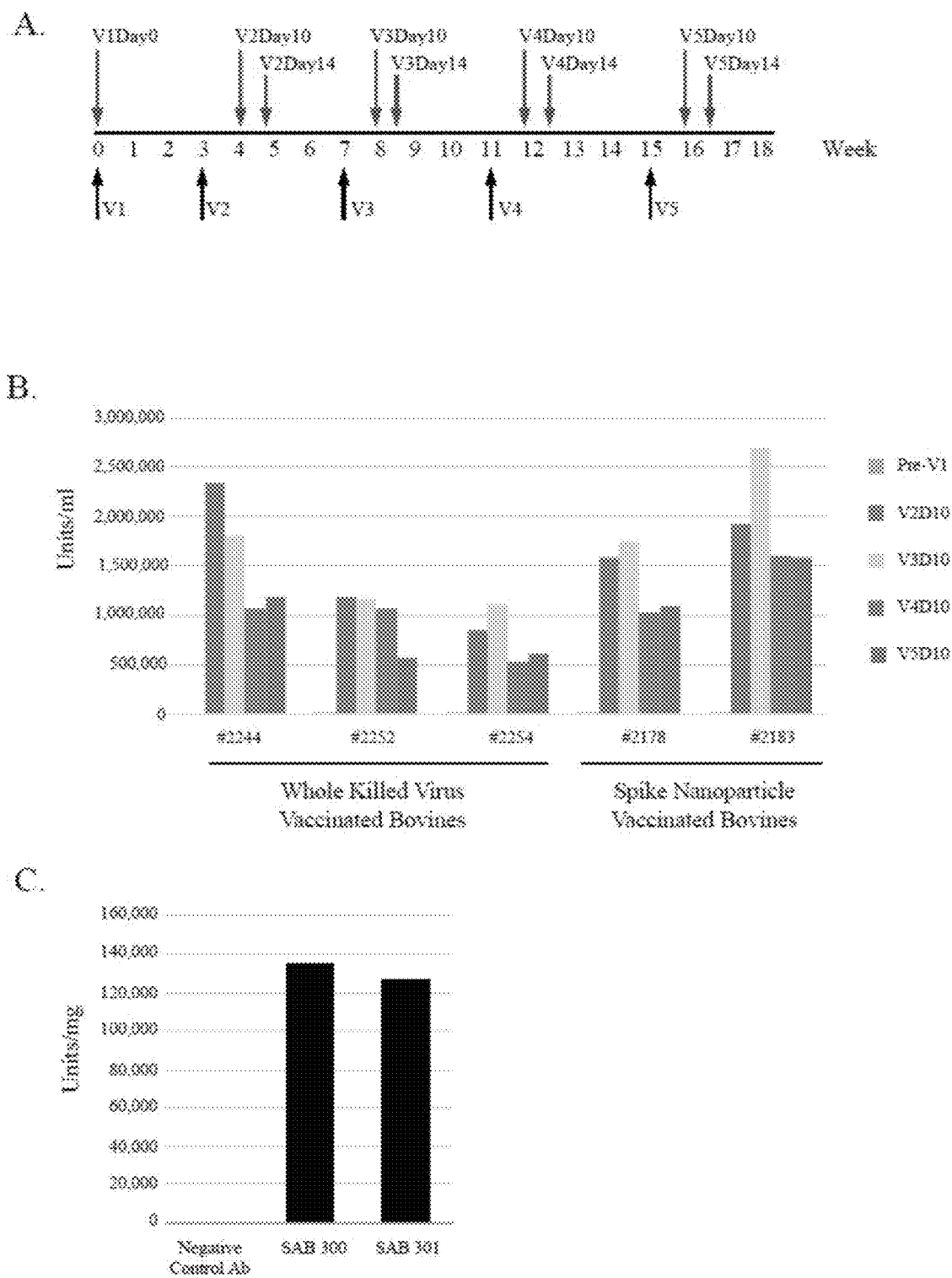
FIG. 10A-C shows a MERS spike protein specific antibody production and ELISA titers. Panel A shows the Vaccination strategy (v notes the vaccination number; e.g. v1 is the first vaccination, v2 is the second vaccination, etc). Panel B shows the antibody titers against recombinant MERS-CoV Spike protein in the serum samples from individual Tc animals over immunization period as measured by ELISA. The titer value (units/ml) is defined as the highest dilution of serum sample where the OD450 reading was 2.5-fold higher than blank. Panel C shows the antibody titers against recombinant MRS-CoV Spike protein in SAB-300 and SAB-301. The titer activity value (units/mg) is defined as the highest dilution of 1 mg of antibody where the OD450 reading was 2.5-fold higher than blank.

MERS-CoV Spike protein specific ELISAs were performed to evaluate the antigen-specific hIgG response in Tc bovines following the immunization with WKV or SN (FIG. 10B) and SAB-300 and SAB-301 (FIG. 10C). The ELISA results demonstrated robust MERS-CoV spike-specific hIgG response at the second vaccination (V2) and maintained high titers through the last immunization (V5) for both the serum and SAB-300 and SAB-301 (FIG. 10). This data indicate that high titer hIgG antibodies targeting MERS-CoV proteins were generated from the Tc bovines immunized with WKV or SN and that both immunoglobulins retained activity after purification.

In Vitro Neutralization of MERS-CoV by Sera, SAB-300 and SAB-301

Fluorescence Reduction Neutralizing Test-50% Reduction (FRNT$_{50}$).

Two neutralization assays were performed to identify the neutralization potential of SAB-300 and SAB-301 in vitro. Sera from vaccinated bovine, SAB-300, and SAB-301 were assayed for their ability to inhibit infection of MERS-CoV in vitro using a Fluorescence Reduction Neutralizing Test (FRNT$_{50}$) and a viral infection neutralization assay. The FRNT assay reports infection using fluorescence and the viral infection neutralization assay reports using cell viability.

Figure 11:
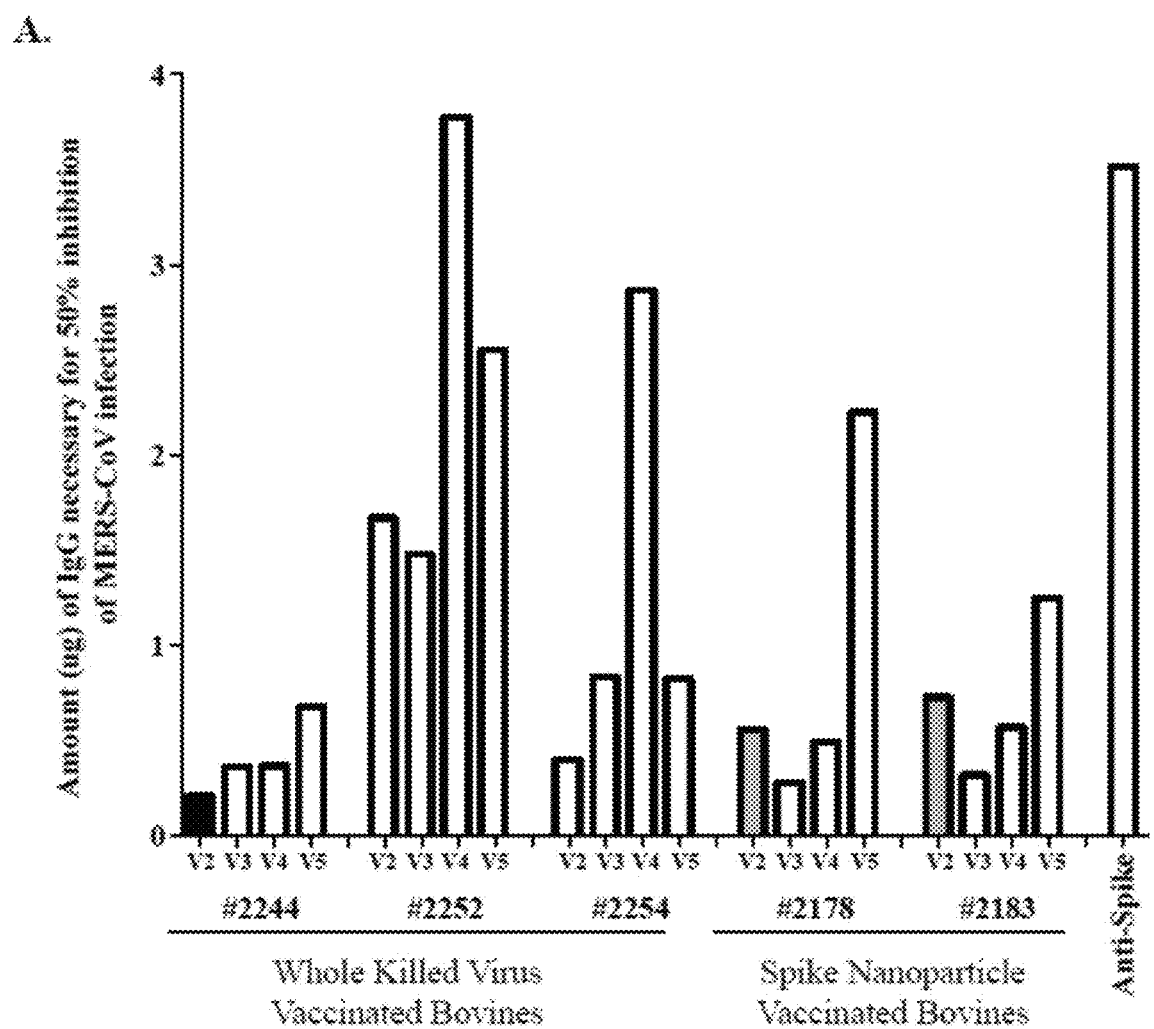
FIG. 11A-B shows the results from a Fluorescence reduction neutralization assay. Panel A shows vaccinated bovine sera was tested for neutralization by $FRNT_{50}$ assay. Mass (μg) of serum needed for 50% inhibition of MERS-CoV detected is graphed for each sample. Infection was quantified after pre-treatment of MERS-CoV with a dilution of sera. After infection, cells were fixed and labeled with anti-spike antibody to quantify the level at which only 50% of the cells were infected compared to mock sera. Panel B shows the $FRNT_{50}$ assay results for SAB-300 and SAB-301 which were assayed for their ability to inhibit infection of MERS-CoV in Vero cells. Antigen affinity purified rabbit Anti-Spike antibody was used as the positive control in these $FRNT_{50}$ assays. Stats: unpaired T-test with Welch's correction, assumed Gaussian distribution. No significance found. Bars are 95% CI
Figure 11:
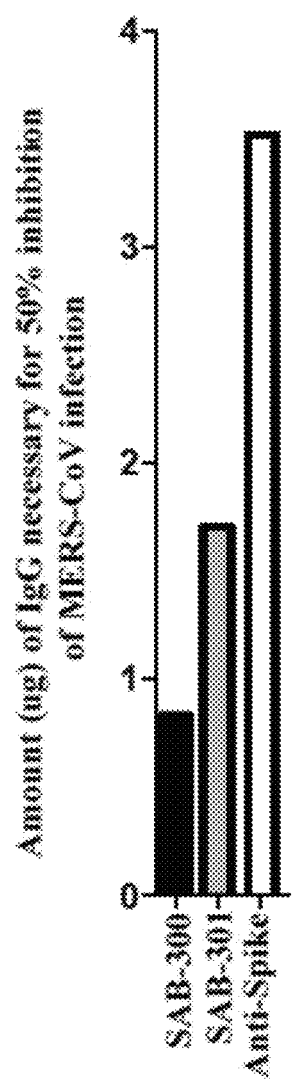

The FRNT$_{50}$ assay was performed on sera from vaccinated bovines (FIG. 11A), and SAB-300 and SAB-301 (FIG. 11B). We find that bovine #2244 V2 produced high titer neutralizing antibody as did V2 from bovines #2178 and #2183. When compared to an equal amount of the positive control Anti-Spike rabbit antibody that is antigen affinity purified, Tc bovine V2 sera are significantly more neutralizing. This data is consistent with the antigen-specific ELISA results in FIG. 10B. SAB-300, purified hIgG from bovine #2244 V2, and SAB-301, purified hIgG from V2 of #2178 and #2183, were then tested for neutralization in the same FRNT$_{50}$ assay. The data demonstrate that SAB-300 and SAB-301 generated similar high levels of neutralizing antibody titers (FIG. 11C). Compared to the equal amounts of a positive control antigen affinity purified a rabbit Anti-Spike antibody, both purified hIgG preparations were highly effective at neutralizing MERS-CoV demonstrating that both SAB-300 and SAB-301 were able to inhibit infection of MERS-CoV in vitro.

Figure 12:
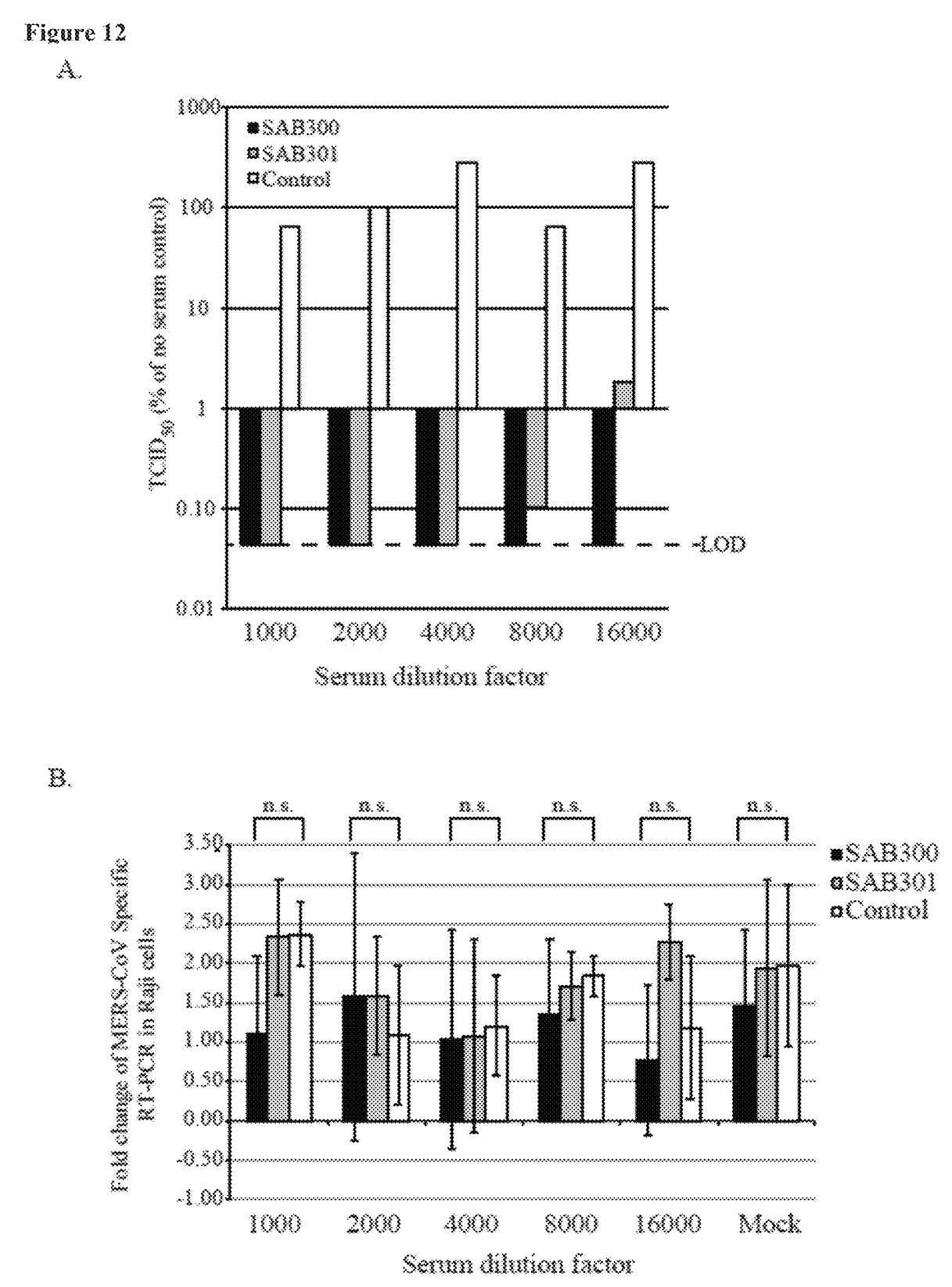

Additionally, SAB-300 and SAB-301 caused significant neutralization of MERS-CoV grown in Vero E6 cells, whereas the no-specific control serum had no significant effect on MERS-CoV infection of Vero E6 cells (FIG. 12A). Levels of infectious MERS-CoV released from cells infected with MERS-CoV pre-treated with SAB-300 were below the detection limit of the assay (158 TCID$_{50}$/ml; FIG. 12A) indicating that SAB-300 is a very strong neutralizing antibody. Levels of infectious MERS-CoV released from cells infected with MERS-CoV pre-treated with SAB-301 were below the detection limit of the assay (158 TCID$_{50}$/ml; FIG. 12A) at all dilutions except 1:8000 and 1:16000 suggesting that serum SAB-301 is a strong neutralizing antibody, but not as inhibitory as SAB-300.

SAB-300 and SAB-301 do not Cause Antibody Enhancement of MERS-CoV

To demonstrate that MERS-CoV viruses bound by antibodies do not allow for entry of the virion into cells that are normally not infected, Raji cells, an immortalized human B cell line that is not typically infected by MERS-CoV, were tested to see if the presence of anti-MERS antibodies could allow for transcription of viral RNA and release of live virus. Raji cells were infected with MERS-CoV pre-incubated with SAB-300 and SAB-301 (FIG. 12B). RT-PCR for viral mRNA and TCID$_{50}$ assays were performed on the media at 48 hours post infection to assess infection. The TCID50 assay could not detect MERS-CoV released from the Raji cells indicating they were not infected by MERS-CoV. Conversely, this assay found that similarly treated Vero E6 cells, which are typically infected by MERS-CoV, produce high levels of virus at 48 hours post infection (data not shown). To determine if MERS-CoV RNA was detected in Raji cells infected with MERS-CoV after pre-incubation with SAB-300 and SAB-301. RNA was extracted from infected cells and analyzed by Taqman realtime PCR with primers specific to MERS-CoV newly transcribed RNA (leader primer) (FIG. 12B). There was no significant detection of MERS-CoV newly transcribed viral RNA (leader primer set) in Raji cells infected with MERS-CoV alone, infected with the non-specific negative control hIgG purified from pre-vaccination plasma, or with cells infected with MERS-CoV pre-treated with SAB-300 or SAB-301. These data demonstrate that there is no antibody dependent enhancement of MERS-CoV infection caused by SAB-300 or SAB-301.

Inhibition of MERS-CoV Replication In Vivo

Figure 13:
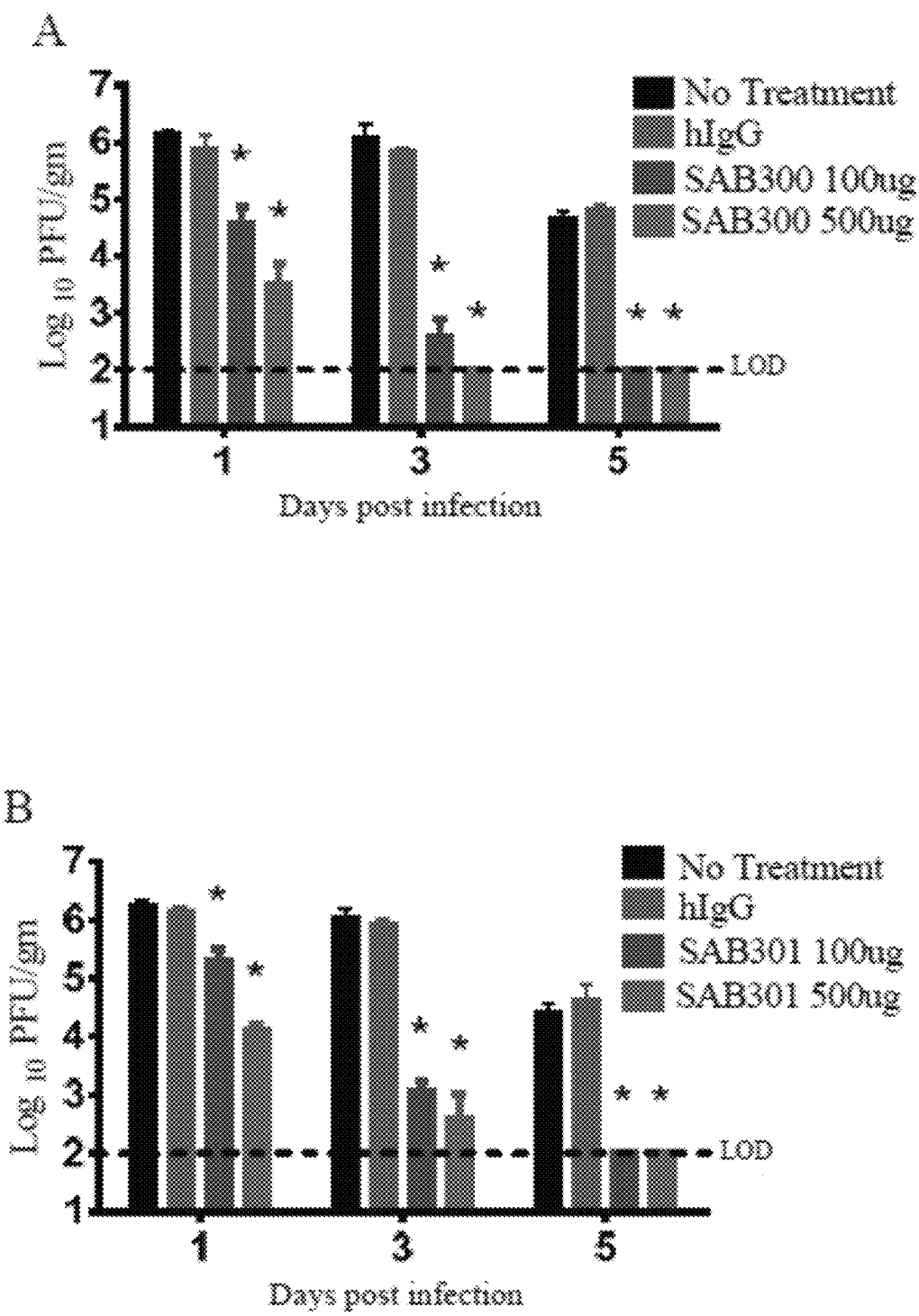
FIG. 13A-B shows inhibition of MERS-CoV replication in vivo. SAB-300 (A) or SAB-301 (B) was transferred into Ad5-hDPP4 transduced BALB/c mice (6 wks, female) intraperitoneally 12 hours before MERS-CoV infection. Mice were then infected with $1\times10^5$ PFU MERS-CoV intranasally. Virus titers in the lungs were measured at the indicated time points. Titers are expressed as PFU/g tissue. n=3 mice/group/time point. *$P<0.05$ compared to No Treatment group; $P<0.05$ compared to Control Ab group.

We tested the efficacy of SAB-300 and SAB-301 in a mouse model of MERS-CoV. Mice are non-permissive to MERS-CoV; however, when transduced with an adenovirus expressing the MERS-CoV receptor, human Dipeptidyl peptidase 4 (hDPP4), they become permissive and replicate virus (Zhao, et al., Proc Natl Acad Sci USA, 2014. 111(13): p. 4970-5). To test the anti-viral activity of the Tc antibodies, BALB/c mice (6-8 weeks) were transduced intranasally with $2.5 \times 10^8$ PFU of Ad5-hDPP4 in 75 ul PBS. At 5 days post transduction, mice were treated by intraperitoneal injection with a single 100 or 500 µs dose of control hIgG, SAB-300 or SAB-301. Twelve hours later, mice were infected intranasally with MERS-CoV ($1 \times 10^5$ PFU) in a total volume of 50 µl. No additional antibody injections were given over the 5-day course of the infection. At 1, 3 and 5 days post infection mice were euthanized and their lungs were dissected. To obtain virus titers, lungs were homogenized in PBS using a manual homogenizer, clarified by centrifugation and titered on Vero cells (FIG. 13). Titers of $\sim 1 \times 10^6$ PFU/mg of lung tissue were found in the lungs of the no treatment group, and the group receiving negative control human IgG at days 1 and 3 post infection with titers dropping to $1 \times 10^5$ at 5 dpi. Mice injected with either 100 µs or 500 µs of SAB-300, ~50-fold or 500-fold reductions, respectively, had virus titers was found at day 1 post infection compared to the hIgG control injection group (FIG. 13A). By day 3 post infection, the reduction in virus titer for the 100 µg group was ~5000-fold while titers in the mice receiving 50 ug were below the level of detection. At 5 days post infection, virus titers in both treated groups were below the level of detection (FIG. 13A). Similar reductions in virus titer were found for the SAB-301 antibody, except that lung titers were modestly higher at day 1 post infection compared to the SAB-300 treated mice (FIG. 13B). By day 5 post infection, all SAB-301 treated mice had virus titers below the level of detection (FIG. 13B). These data demonstrate that both SAB-300 and SAB-301 were able to protect mice from MERS-CoV infection with a single prophylactic injection.

EXAMPLE 4

Figure 14:
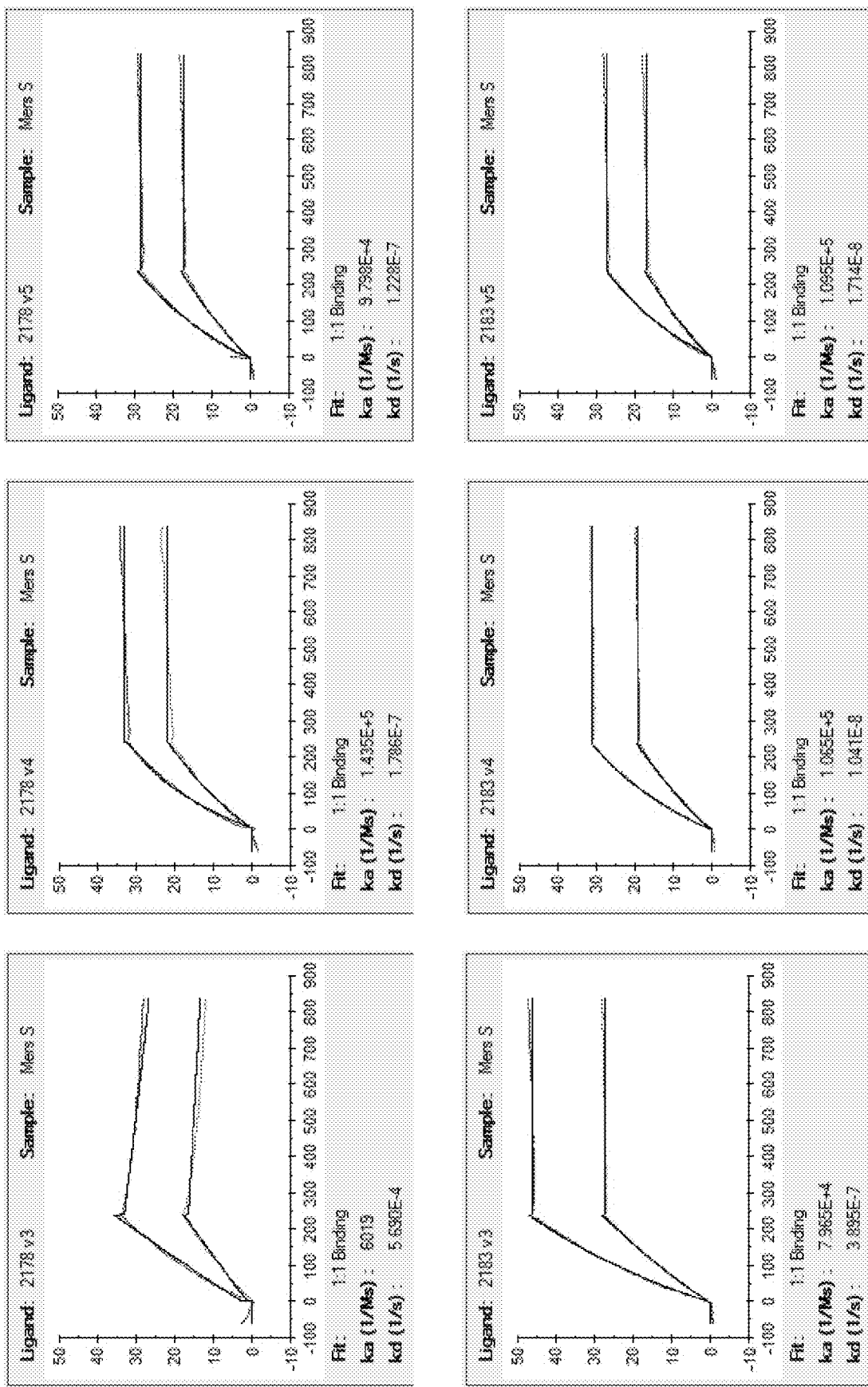
FIG. 14 shows the binding kinetics of MERS-CoV S protein to bovine Tc derived human IgG.

BIACORE Analysis of Antibodies in Animals Immunized with MERS-CoV Spike Protein (S) Nanoparticles The avidity of two antibodies from two Tc bovine (#2178 and 2183) immunized with the MERS-CoV S nanoparticle vaccine following a series of immunizations as shown in FIG. 10A and Example 3 was tested by anti-S affinity (Biacore™) analysis. We tested the avidity of antibodies in the serum of these animals after vaccination 3 (v3), vaccination 4 (v4), and vaccination 5 (v5). Briefly, using a protein A/G amine coupled to a CM5 chip, the bovine Tc serum IgG was captured to the flow cell. MERS Spike protein antigen at 0, 20, and 40 nM was injected to the flow cell for 180 seconds and followed by disassociation for 600 seconds. The 1:1 fit model was applied. Association and dissociation rates were measured as a function of time and plotted on a sensorgram, and the dissociation constant was calculated from the association and dissociation rates. The results are shown in FIG. 14 and Table 1.

TABLE 1

Binding kinetics of MERS-CoV S antigen to Tc human IgG from bovines

| serum samples | $k_{on}$ (Ms) | $k_{off}$ (/s) | $K_D$ (M) |
|---|---|---|---|
| 2178 v3 | 6019 | $5.69 \times 10^{-4}$ | $9.45 \times 10^{-8}$ |
| 2178 v4 | $1.44 \times 10^5$ | $1.79 \times 10^{-7}$ | $1.24 \times 10^{-12}$ |
| 2178 v5 | $9.80 \times 10^4$ | $1.23 \times 10^{-7}$ | $1.25 \times 10^{-12}$ |
| 2183 v3 | $7.97 \times 10^4$ | $3.90 \times 10^{-7}$ | $4.89 \times 10^{-12}$ |
| 2183 v4 | $1.07 \times 10^5$ | $1.04 \times 10^{-8}$ | $9.78 \times 10^{-14}$ |
| 2183 v5 | $1.10 \times 10^5$ | $1.71 \times 10^{-8}$ | $1.57 \times 10^{-13}$ |

Table 2 shows the affinity of anti-S1 mAbs produced by phage-display as disclosed in Ying et al. J. Virol. (2014). A comparison of the data in these two tables demonstrates that the reported $K_D$ and antibody $K_{off}$ rates of the MERS-CoV mAbs produced through phage display are orders of magnitude less than the polyclonal anti-S responses induced in the Tc bovine.

TABLE 2

Binding kinetics of mAb to MERS-CoV RBD (Ying et al. (2014))

| mAb | $k_{on}$ (Ms) | $k_{off}$ (/s) | $K_D$ (M) |
|---|---|---|---|
| m336 | $1.66 \times 10^6$ | $1.65 \times 10^{-4}$ | $9.94 \times 10^{-11}$ |
| m337 | $1.87 \times 10^5$ | $1.54 \times 10^{-4}$ | $8.24 \times 10^{-10}$ |
| m338 | $3.55 \times 10^5$ | $1.98 \times 10^{-4}$ | $5.58 \times 10^{-10}$ |

OTHER EMBODIMENTS

Those skilled in the art will recognize, or be able to ascertain using no more than routine experimentation, many equivalents to the specific embodiments described herein. Such equivalents are intended to be encompassed by the claims provided herein.

INCORPORATION BY REFERENCE

This application incorporates by reference all publications or references disclosed herein for all purposes in their entireties.

This application incorporates by reference for all purposes the entirety of the following: U.S. Ser. No. 12/306,965, filed Jun. 27, 2007, U.S. Ser. No. 61/015,440 filed on Dec. 20, 2007, U.S. Ser. No. 11/582,540, filed Oct. 18, 2006, U.S. Ser. No. 12/633,995, filed Oct. 18, 2006 U.S. Ser. No. 60/727,513, filed Oct. 18, 2005; 60/780,847, filed Mar. 10, 2006; 60/800,006, filed May 15, 2006; 60/831,196, filed Jul. 17, 2006; 60/832,116, filed Jul. 21, 2006, and 60/845,495, filed Sep. 19, 2006, and Ser. No. 10/617,569, filed Jul. 11, 2003.

REFERENCES

1. Berglund, P., Fleeton, M. N., Smerdou, C., and Liljestrom, P. (1999). Immunization with recombinant Semliki Forest virus induces protection against influenza challenge in mice. Vaccine 17, 497-507.
2. Cox, J. C., and Coulter, A. R. (1997). Adjuvants—a classification and review of their modes of action. Vaccine 15, 248-256.
3. Crawford, J., Wilkinson, B., Vosnesensky, A., Smith, G., Garcia, M., Stone, H., and Perdue, M. L. (1999). Baculovirus-derived hemagglutinin vaccines protect against lethal influenza infections by avian H5 and H7 subtypes. Vaccine 17, 2265-2274.
4. Crowther R A, Kiselev N A, Bottcher B, Berriman J A, Borisova G P, Ose V, Pumpens P. (1994). Three-dimensional structure of hepatitis B virus core particles determined by electron cryomicroscopy. Cell 17, 943-50.
5. Gomez-Puertas, P., Mena, I., Castillo, M., Vivo, A., Perez-Pastrana, E., and Portela, A. (1999). Efficient formation of influenza virus-like particles: dependence on the expression levels of viral proteins. J. Gen. Virol. 80, 1635-1645.
6. Johansson, B. E. (1999). Immunization with influenza A virus hemagglutinin and neuraminidase produced in recombinant baculovirus results in a balanced and broadened immune response superior to conventional vaccine. Vaccine 17, 2073-2080.
7. Lakey, D. L., Treanor, J. J., Betts, B. F., Smith, G. E., Thompson, J., Sannella, E., Reed, G., Wilkinson, B. E., and Wright, P. E. (1996) Recombinant baculovirus influenza A hemagglutinin vaccines are well tolerated and immunogenic in healthy adults. J. Infect. Dis. 174, 838-841.
8. Latham, T., and Galarza, J. M. (2001). Formation of wild-type and chimeric influenza virus-like particles following simultaneous expression of only four structural proteins. J. Virol. 75, 6154-6165.
9. Mena, I., Vivo, A., Perez, E., and Portela, A (1996). Rescue of a synthetic chloramphenicol acetyltransferase RNA into influenza-like particles obtained from recombinant plasmids. J. Virol. 70, 5016-5024.
10. Murphy, B. R., and Webster, R. G. (1996). Orthomyxoviruses. In "Virology" (D. M. K. B. N. Fields, P. M. Howley, Eds.) Vol. 1, pp. 1397-1445. Lippincott-Raven, Philadelphia.
11. Neumann, G., Watanabe, T., and Kawaoka, Y. (2000). Plasmid-driven formation of influenza virus-like particles. J. Virol. 74, 547-551.
12. Olsen, C. W., McGregor, M. W., Dybdahl-Sissoko, N., Schram, B. R., Nelson, K. M., Lunn, D. P., Macklin, M. D., and Swain, W. F. (1997). Immunogenicity and efficacy of baculovirus-expressed and DNA-based equine influenza virus hemagglutinin vaccines in mice. Vaccine 15, 1149-1156.
13. Peiris, J. S., Guan, Y., Markwell, D., Ghose, P., Webster, R. G., and Shortridge, K. F. (2001). Cocirculation of avian H9N2 and contemporary "human" H3N2 influenza A viruses in pigs in southwestern China: potential for genetic reassortment? J. Virol. 75, 9679-9686.
14. Pumpens, P., and Grens, E. (2003). Artificial genes for chimeric virus-like particles. In: "Artificial DNA" (Khudyakov, Y. E, and Fields, H. A., Eds.) pp. 249-327. CRC Press, New York.
15. Pushko, P., Parker, M., Ludwig, G. V., Davis, N. L., Johnston, R. E., and Smith, J. F. (1997). Replicon-helper systems from attenuated Venezuelan equine encephalitis virus: expression of heterologous genes in vitro and immunization against heterologous pathogens in vivo. Virology 239, 389-401.
16. Slepushkin, V. A., Katz, J. M., Black, R. A., Gamble, W. C., Rota, P. A., and Cox, N. J. (1995). Protection of mice against influenza A virus challenged by vaccination with baculovirus-expressed M2 protein. Vaccine 13, 1399-1402.
17. Treanor, J. J., Betts, R. F., Smith, G. E., Anderson, E. L., Hackett, C. S., Wilkinson, B. E., Belshe, R. B., and Powers, D. C. (1996). Evaluation of a recombinant hemagglutinin expressed in insect cells as an influenza vaccine in young and elderly adults. J. Infect. Dis. 173, 1467-1470.
18. Tsuji, M., et al. (1998). Recombinant Sindbis viruses expressing a cytotoxic T-lymphocyte epitope of a malaria parasite or of influenza virus elicit protection against the corresponding pathogen in mice. J. Virol. 72, 6907-6910.
19. Ulmer, J. B., et al. (1993). Heterologous protection against influenza by injection of DNA encoding a viral protein. Science 259, 1745-1749.
20. Ulmer, J. B., et al. (1998). Protective CD4+ and CD8+T cells against influenza virus induced by vaccination with nucleoprotein DNA. J. Virol. 72, 5648-5653.
21. Watanabe, T., Watanabe, S., Neumann, G., and Kawaoka, Y. (2002) Immunogenicity and protective efficacy of replication-incompetent influenza virus-like particles. J. Virol. 76, 767-773.
22. Zhou, X., et al. (1995). Generation of cytotoxic and humoral immune responses by non-replicative recombinant Semliki Forest virus. Proc. Natl. Acad. Sci. USA 92, 3009-3013.
23. Zabel et al. (2014). Viral Particles Drive Rapid Differentiation of Memory B Cells into Secondary Plasma Cells Producing Increased Levels of Antibodies. J. Immunol. 192:5499-5508.
24. Zhang et al. (2000). HPV6b virus like particles are potent immunogens without adjuvant in man. Vaccine. 18:1051-8.

We claim:

1. An immunogenic composition comprising
   (i) a MERS-CoV nanoparticle, wherein the nanoparticle comprises a MERS CoV antigen, wherein the antigen consists of baculovirus-expressed full-length Spike polypeptide in trimer form; and wherein the Spike polypeptide is the only polypeptide in the nanoparticle, and
   (ii) an adjuvant, wherein the adjuvant consists of two ISCOM matrix particle types wherein the first particle type comprises a lipid and saponin Fraction A from *Quillaja Saponaria* Molina, and the second particle type comprises a lipid and saponin Fraction C from *Quillaja Saponaria* Molina;
   wherein the composition is capable of inducing neutralizing antibodies against MERS-CoV.

2. The composition of claim 1, wherein the concentration of the nanoparticle is about 20 μg/mL to about 60 μg/mL.

3. The composition of claim 2, wherein the concentration of the nanoparticle is about 30 μg/mL to about 50 μg/mL.

4. The composition of claim 1, wherein the Spike polypeptide consists of SEQ ID NO: 2.

5. A method of producing a high affinity antibody comprising administering to an animal an immunogenic composition of claim 1, collecting serum and/or plasma from the animal, and purifying the antibody from the serum and/or plasma.

6. The composition of claim 5, wherein the nanoparticle comprises about five trimers to about 30 trimers of the Spike polypeptide.

7. The composition of claim 6, wherein the nanoparticle comprises about ten trimers to about 20 trimers of the Spike polypeptide.

8. The composition of claim 5, wherein the concentration of the nanoparticle is about 20 μg/mL to about 60 μg/mL.

9. The composition of claim 8 wherein the concentration of the nanoparticle is about 30 μg/mL to about 50 μg/mL.

10. The composition of claim 5, wherein the Spike polypeptide comprises SEQ ID NO: 2.

11. The composition of claim 5, wherein the Spike polypeptide consists of SEQ ID NO: 2.

12. The method of claim 5, comprising the administration of an adjuvant.

13. The method of claim 12, wherein the adjuvant is selected from the group consisting of Montanide ISA 206, Quil A, Alum, Freund's adjuvant, incomplete Freund's adjuvant, and aluminum hydroxide adjuvants.

14. The method of claim 5, wherein the animal is bovine or equine.

15. The method of claim 14, where the bovine or equine animal is a transgenic animal.

16. The method of claim 5, wherein the antibody has a KD between $10^{-8}$ and $10^{-15}$.

17. The method of claim 16, wherein the antibody has a KD between $10^{-12}$ and $10^{-14}$.

18. The method of claim 5, comprising administering the purified high affinity antibody to a human subject.

* * * * *

UNITED STATES PATENT AND TRADEMARK OFFICE
CERTIFICATE OF CORRECTION

PATENT NO. : 10,751,410 B2  
APPLICATION NO. : 15/023629  
DATED : August 25, 2020  
INVENTOR(S) : Smith et al.

Page 1 of 2

It is certified that error appears in the above-identified patent and that said Letters Patent is hereby corrected as shown below:

In the Claims

At Claim 6, Column 39, Line 28, replace:
"The composition of claim 5, wherein the nanoparticle comprises about five trimers to about 30 trimers of the Spike polypeptide."
With:
--The method of claim 5, wherein the nanoparticle of the immunogenic composition comprises about five trimers to about 30 trimers of the Spike polypeptide.--

At Claim 7, Column 40, Line 1, replace:
"The composition of claim 6, wherein the nanoparticle comprises about ten trimers to about 20 trimers of the Spike polypeptide."
With:
--The method of claim 6, wherein the nanoparticle of the immunogenic composition comprises about ten trimers to about 20 trimers of the Spike polypeptide.--

At Claim 8, Column 40, Line 4, replace:
"The composition of claim 5, wherein the concentration of the nanoparticle is about 20 µg/mL to about 60 µg/mL."
With:
--The method of claim 5, wherein the concentration of the nanoparticle in the immunogenic composition is about 20 µg/mL to about 60 µg/mL.--

At Claim 9, Column 40, Line 6, replace:
"The composition of claim 8 wherein the concentration of the nanoparticle is about 30 µg/mL to about 50 µg/mL."
With:
--The method of claim 8, wherein the concentration of the nanoparticle in the immunogenic composition is about 30 µg/mL to about 50 µg/mL.--

Signed and Sealed this  
Fifteenth Day of February, 2022

Drew Hirshfeld  
*Performing the Functions and Duties of the  
Under Secretary of Commerce for Intellectual Property and  
Director of the United States Patent and Trademark Office*

CERTIFICATE OF CORRECTION (continued)
U.S. Pat. No. 10,751,410 B2

At Claim 10, Column 40, Line 8, replace:
"The composition of claim 5, wherein the Spike polypeptide comprises SEQ ID NO: 2."
With:
--The method of claim 5, wherein the Spike polypeptide in the immunogenic composition comprises SEQ ID NO: 2.--

At Claim 11, Column 40, Line 10, replace:
"The composition of claim 5, wherein the Spike polypeptide consists of SEQ ID NO: 2."
With:
--The method of claim 5, wherein the Spike polypeptide in the immunogenic composition consists of SEQ ID NO: 2.--